(12) United States Patent
Chakroff et al.

(10) Patent No.: US 12,201,648 B2
(45) Date of Patent: *Jan. 21, 2025

(54) METHODS OF TREATING CHRONIC WOUNDS USING ELECTROSPUN FIBERS

(71) Applicant: NFS IP Holdings, LLC, Dublin, OH (US)

(72) Inventors: Jason Chakroff, Columbus, OH (US); Ronald Lloyd Bracken, Monroe, GA (US); Jed Johnson, London, OH (US)

(73) Assignee: NFS IP Holdings, LLC, Dublin, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/152,240

(22) Filed: Jan. 10, 2023

(65) Prior Publication Data

US 2023/0285445 A1 Sep. 14, 2023

Related U.S. Application Data

(63) Continuation of application No. 16/710,603, filed on Dec. 11, 2019, now Pat. No. 11,576,927.

(60) Provisional application No. 62/778,024, filed on Dec. 11, 2018.

(51) Int. Cl.
*A61K 31/765* (2006.01)
*A61P 17/02* (2006.01)

(52) U.S. Cl.
CPC ............ *A61K 31/765* (2013.01); *A61P 17/02* (2018.01)

(58) Field of Classification Search
CPC ............................. A61K 31/765; A61P 17/02
See application file for complete search history.

(56) References Cited

U.S. PATENT DOCUMENTS

| | | |
|---|---|---|
| 4,738,740 A | 4/1988 | Pinchuk et al. |
| 5,258,027 A | 11/1993 | Berghaus |
| 5,388,588 A | 2/1995 | Nabai et al. |
| 5,441,491 A | 8/1995 | Verschoor et al. |
| 5,628,788 A | 5/1997 | Pinchuk |
| 6,143,022 A | 11/2000 | Shull et al. |
| 6,143,293 A | 11/2000 | Weiss et al. |
| 6,592,623 B1 | 7/2003 | Bowlin et al. |
| 6,635,082 B1 | 10/2003 | Hossainy et al. |
| 6,846,320 B2 | 1/2005 | Ashby et al. |
| 7,115,220 B2 | 10/2006 | Dubson et al. |
| 7,172,765 B2 | 2/2007 | Chu et al. |
| 7,220,281 B2 | 5/2007 | Lambrecht et al. |
| 7,390,760 B1 | 6/2008 | Chen et al. |
| 7,490,563 B2 | 2/2009 | Eastin et al. |
| 7,629,030 B2 | 12/2009 | Robertson et al. |
| 7,718,351 B2 | 5/2010 | Ying et al. |
| 7,993,567 B2 | 8/2011 | Scott-Carnell et al. |
| 8,157,722 B2 | 4/2012 | Arnal et al. |
| 8,222,166 B2 | 7/2012 | Chu et al. |
| 8,728,463 B2 | 5/2014 | Atala et al. |
| 9,334,476 B2 | 5/2016 | Arinzeh et al. |
| 9,737,632 B2 | 8/2017 | Johnson et al. |
| 9,771,557 B2 | 9/2017 | Arinzeh et al. |
| 10,080,687 B2 | 9/2018 | MacEwan |
| 10,562,225 B2 | 2/2020 | Johnson |
| 10,617,512 B2 | 4/2020 | MacEwan et al. |
| 10,632,228 B2 | 4/2020 | MacEwan |
| 10,682,444 B2 | 6/2020 | MacEwan |
| 10,888,409 B2 | 1/2021 | MacEwan et al. |
| 11,576,927 B2 | 2/2023 | Chakroff et al. |
| 2002/0090725 A1 | 7/2002 | Simpson et al. |
| 2002/0142458 A1 | 10/2002 | Williams et al. |
| 2003/0168756 A1 | 9/2003 | Balkus, Jr. et al. |
| 2003/0211130 A1 | 11/2003 | Sanders et al. |
| 2003/0226750 A1 | 12/2003 | Fenn |
| 2004/0037813 A1 | 2/2004 | Simpson et al. |
| 2005/0084958 A1 | 4/2005 | Vein |
| 2005/0177249 A1 | 8/2005 | Kladakis et al. |
| 2005/0277985 A1 | 12/2005 | Wert et al. |
| 2006/0060999 A1 | 3/2006 | Amagasa et al. |
| 2006/0085063 A1 | 4/2006 | Shastri et al. |
| 2006/0128012 A1 | 6/2006 | Arinzeh et al. |

(Continued)

FOREIGN PATENT DOCUMENTS

| | | |
|---|---|---|
| CN | 101641121 A | 2/2010 |
| CN | 102008755 A | 4/2011 |

(Continued)

OTHER PUBLICATIONS

Krzyszczyk et al. Frontiers in Physiology (2018).*
Canton et al. Microbiology of the cell ; 25(21) 2014.*
Agudelo-Garcia et al. "Glioma Cell Migration on Three-dimensional Nanofiber Scaffolds is Regulated by Substrate Topography and Abolished by Inhibition of STAT3 Signaling 1.2" Sep. 2011, NeoPlasia 13(9):831-840.
Ayres et al. "Microvascular Endothelial Cell Migration in Scaffolds of Electrospun Collagen" Mar. 2005, Wound Repair and Regeneration 13(2):3 Pages A6 (abstract only).
Baker et al. "The Potential to Improve Cell Infiltration in Composite Fiber-Aligned Electrospun Scaffolds by the Selective Removal of Sacrificial Fibers" May 2008, Biomaterials, Elsevier 29(15):2348-2358, DOI: 10.1016/j.biomaterials.2008.01.032.

(Continued)

*Primary Examiner* — Shirley V Gembeh
(74) *Attorney, Agent, or Firm* — DLA Piper LLP (US)

(57) ABSTRACT

A method of treating a chronic wound may comprise applying to the wound a first scaffold comprising an electrospun polymer fiber. The electrospun fiber may comprise a polymer selected from the group consisting of polyglycolic acid, poly(lactide-co-caprolactone), polylactic acid, polycaprolactone, copolymers thereof, and combinations thereof. The first scaffold may have a thickness from about 50 μm to about 1 mm, a length from about 1 cm to about 20 cm, and a width from about 1 cm to about 15 cm. The method may further comprise keeping the first scaffold on the chronic wound for a time period of about 3 days to about 21 days. After the time period passes, the chronic wound may have a decreased planimetric area.

11 Claims, 38 Drawing Sheets

(56) References Cited

U.S. PATENT DOCUMENTS

| | | |
|---|---|---|
| 2006/0134157 A1 | 6/2006 | Lehman et al. |
| 2006/0135020 A1 | 6/2006 | Weinberg et al. |
| 2006/0154063 A1 | 7/2006 | Fujihara et al. |
| 2006/0204539 A1 | 9/2006 | Atala et al. |
| 2007/0142907 A1 | 6/2007 | Moaddeb et al. |
| 2007/0191956 A1 | 8/2007 | Prewett et al. |
| 2007/0218118 A1 | 9/2007 | Michal et al. |
| 2007/0232169 A1 | 10/2007 | Strickler et al. |
| 2007/0269481 A1 | 11/2007 | Li et al. |
| 2007/0286880 A1 | 12/2007 | Vasiliev et al. |
| 2008/0208323 A1 | 8/2008 | El-Kurdi et al. |
| 2008/0208358 A1 | 8/2008 | Bellamkonda et al. |
| 2009/0018643 A1 | 1/2009 | Hashi et al. |
| 2009/0074832 A1 | 3/2009 | Zussman et al. |
| 2009/0108503 A1 | 4/2009 | Scott-Carnell et al. |
| 2009/0143855 A1 | 6/2009 | Weber et al. |
| 2009/0152773 A1 | 6/2009 | Barinov et al. |
| 2009/0162468 A1 | 6/2009 | Barinov et al. |
| 2009/0208577 A1 | 8/2009 | Xu et al. |
| 2009/0253328 A1 | 10/2009 | Watanabe et al. |
| 2010/0082114 A1 | 4/2010 | Gingras et al. |
| 2010/0105799 A1 | 4/2010 | Rudd et al. |
| 2010/0166854 A1 | 7/2010 | Michniak-Kohn et al. |
| 2010/0222771 A1 | 9/2010 | Mitchell et al. |
| 2010/0233115 A1 | 9/2010 | Patel et al. |
| 2010/0273258 A1 | 10/2010 | Lannutti et al. |
| 2010/0303881 A1 | 12/2010 | Hoke et al. |
| 2011/0022149 A1 | 1/2011 | Cox et al. |
| 2011/0028834 A1 | 2/2011 | Zussman |
| 2011/0030885 A1 | 2/2011 | Anneaux et al. |
| 2011/0070283 A1 | 3/2011 | Hossainy et al. |
| 2011/0083987 A1 | 4/2011 | Rolland et al. |
| 2011/0098826 A1 | 4/2011 | Mauck et al. |
| 2011/0166647 A1 | 7/2011 | Hashi et al. |
| 2011/0177395 A1 | 7/2011 | Kamisasa |
| 2011/0180951 A1 | 7/2011 | Teo et al. |
| 2011/0270412 A1 | 11/2011 | Bellan et al. |
| 2012/0068384 A1 | 3/2012 | Phaneuf et al. |
| 2012/0093717 A1 | 4/2012 | Mauck et al. |
| 2012/0129713 A1 | 5/2012 | Montagu et al. |
| 2012/0208421 A1 | 8/2012 | Qi et al. |
| 2013/0052254 A1 | 2/2013 | Arinzeh et al. |
| 2013/0066438 A1 | 3/2013 | Seifalian |
| 2013/0095165 A1 | 4/2013 | Olson et al. |
| 2013/0103079 A1 | 4/2013 | Lau et al. |
| 2013/0150963 A1 | 6/2013 | Johnson |
| 2013/0245784 A1 | 9/2013 | Tan et al. |
| 2013/0310920 A1 | 11/2013 | Su |
| 2013/0338791 A1 | 12/2013 | McCullen et al. |
| 2014/0030315 A1 | 1/2014 | Johnson |
| 2014/0057346 A1 | 2/2014 | Johnson |
| 2014/0072951 A1 | 3/2014 | Johnson |
| 2014/0079759 A1 | 3/2014 | Patel et al. |
| 2014/0107803 A1 | 4/2014 | Grosse |
| 2014/0272225 A1 | 9/2014 | Johnson |
| 2014/0302121 A1 | 10/2014 | Bevier |
| 2014/0309726 A1 | 10/2014 | Wang |
| 2014/0377213 A1 | 12/2014 | Hong et al. |
| 2015/0010607 A1 | 1/2015 | Francis et al. |
| 2015/0110846 A1 | 4/2015 | Yu et al. |
| 2016/0022873 A1 | 1/2016 | Besner et al. |
| 2016/0024690 A1 | 1/2016 | Francis et al. |
| 2016/0030640 A1 | 2/2016 | Schroeder et al. |
| 2016/0143745 A1 | 5/2016 | Kandel et al. |
| 2016/0317706 A1 | 11/2016 | Johnson |
| 2016/0325015 A1 | 11/2016 | Johnson et al. |
| 2017/0007741 A1 | 1/2017 | D'Lima et al. |
| 2017/0182206 A1 | 6/2017 | Johnson et al. |
| 2017/0306295 A1 | 10/2017 | Hazot et al. |
| 2017/0319742 A1 | 11/2017 | Johnson et al. |
| 2019/0328678 A1 | 10/2019 | Sunderland |
| 2020/0164107 A1 | 5/2020 | Xie et al. |

FOREIGN PATENT DOCUMENTS

| | | |
|---|---|---|
| CN | 102908677 A | 2/2013 |
| CN | 108691028 A | 10/2018 |
| EP | 0416846 A2 | 3/1991 |
| EP | 0552271 B1 | 4/1996 |
| EP | 2422003 A1 | 2/2012 |
| JP | 2011509786 A | 3/2011 |
| JP | 2012505320 A | 3/2012 |
| JP | 2012527217 A | 11/2012 |
| JP | 2013031595 A | 2/2013 |
| WO | 1991018612 A1 | 12/1991 |
| WO | 2001015754 A1 | 3/2001 |
| WO | 2001027365 A1 | 4/2001 |
| WO | 2005012606 A2 | 2/2005 |
| WO | 2006138552 A2 | 12/2006 |
| WO | 2008100556 A2 | 8/2008 |
| WO | 2008118913 A2 | 10/2008 |
| WO | 2008137659 A1 | 11/2008 |
| WO | 2009089035 A1 | 7/2009 |
| WO | 2010040129 A2 | 4/2010 |
| WO | 2010048281 A1 | 4/2010 |
| WO | 2010124207 A1 | 10/2010 |
| WO | 2011142667 A1 | 11/2011 |
| WO | 2013025819 A2 | 2/2013 |
| WO | 2013078051 A1 | 5/2013 |
| WO | 2014031721 A1 | 2/2014 |
| WO | 2014145864 A1 | 9/2014 |
| WO | 2015153011 A1 | 10/2015 |
| WO | 2018162900 A1 | 9/2018 |
| WO | 2020123619 A1 | 6/2020 |

OTHER PUBLICATIONS

Barnhart et al. "Evaluation of an Intra-Articular Synthetic Ligament for Treatment of Cranial Cruciate Ligament Disease in Dogs: A Six-Month Prospective Clinical Trial" Nov. 2016, Veterinary and Comparative Orthopaedics and Traumatology 29:491-498.

Barron et al. "Full-thickness Oesophageal Regeneration in Pig Using a Polyurethane Mucosal Cell Seeded Graft" Jan. 2018, J. of Tissue Engineering and Regenerative Medicine 12(1):11 Pages.

Bershadsky et al. "Adhesion-Mediated Mechanosensitivity: A Time to Experiment, and a Time to theorize" Oct. 2006, Current Opinion in Cell Biology 18(5):472-481.

Best et al. "Designing a Tissue-Engineered Tracheal Scaffold for Preclinical Evaluation" Jan. 2018, International Journal of Pediatric Otorhinolaryngology 104:155-160.

Best et al. "Oversized Biodegradable Arterial Grafts Promote Enhanced Neointimal Tissue Formation" Aug. 2018, Tissue Engineering: Part A, 24(15-16):1251-1261.

Boomer et al. "Scaffolding for Challenging Environments: Materials Selection for Tissue Engineered Intestine" Nov. 2014, J. Biomedical Materials Research Part A 102(11):3795-3802.

Bucala et al. "Circulating Fibrocytes Define a New Leukocyte Subpopulation That Mediates Tissue Repair" Nov. 1994, Molecular Medicine 1 (1 ):71-81.

Cattaruzza et al. "Proteoglycan Control of Cell Movement during Wound Healing and Cancer Spreading" Sep. 2005, Matrix Biology 24(6):400-417.

Chakroff et al. "Development and Characterization of Novel Electrospun Meshes for Hernia Repair" 2015, SOJ Materials Science & Engineering 2(2):1-9.

Chen et al. "Electrospun 3D Fibrous Scaffolds for Chronic Wound Repair" Apr. 6, 2016, Materials 9(272):1-12.

Chen et al. "Preparation and Characterization of Coaxial Electrospun Thermoplastic Polyurethane/Collagen Compound Nanofibers for Tissue Engineering Applications" 2010, Colloids and Surfaces B-Biointerfaces 79 2):315-325.

Cheng et al. "Engineering the Microstructure of Electrospun Fibrous Scaffolds by Microtopography" 2013, BioMacromolecules 14(5):1349-1360.

Chew et al. "The Role of Electrospinning in the Emerging Field of Nanomedicine" 2006, Current Pharmaceutical Design 12(36A):4751-4770.

(56) References Cited

OTHER PUBLICATIONS

Choi et al. "Structuring Electrospun Polycaprolactone Nanofiber Tissue Scaffolds by Femtosecond Laser Ablation" Nov. 2007, J. Laser Applications 19(4):225-231.
Clark et al. "Effect of Cell Seeding on Neotissue Formation in a Tissue Engineered Trachea" Jan. 2016, J. Pediatric Surgery 51(1):49-55.
Cromeens et al. "Production of Tissue-Engineered Intestine from Expanded Enteroids" Jul. 2016, J. Surgical Research 204(01): 164-175.
Cukierman et al. "Taking Cell-matrix Adhesions to the Third Dimension" Nov. 23, 2001, Science 294:1708-1712.
D'Amato et al. "Solvent Retention in Electrospun Fibers Affects Scaffold Mechanical Properties" Feb. 2018, Electrospinning 2(1): 15-28.
Dhandayuthapani et al. "Polymeric Scaffolds in Tissue Engineering Application: A Review" Sep. 11, 2011, International J. Polymer Science 2011(290602):20 Pages.
Dharmadhikari et al. "Deconstructing Tissue Engineered Trachea: Assessing the Role of Synthetic Scaffolds, Segmental Replacement and Cell Seeding on Graft Performance" Jan. 15, 2020, Acta Biomaterialia 102:181-191.
Dharmadhikari et al. "Mouse Model of Tracheal Replacement with Electrospun Nanofiber Scaffolds" May 2019, Annals of Otology, Rhinology & Laryngology 128(5):10 Pages.
Diaz et al. "Controlled Encapsulation of Hydrophobic Liquids in Hydrophilic Polymer Nanofibers by CoElectrospinning" 2006, Advanced Functional Materials 16(16):2110-2116.
Discher et al. "Tissue Cells Feel and Respond to the Stiffness of Their Substrate" Nov. 18, 2005, Science 310:1139-1143.
Drilling et al. "Fabrication of Burst Pressure Competent Vascular Grafts via Electrospinning: Effects of Microstructure" Mar. 15, 2009, J. Biomedical Materials Research Part A 88(4):923-934.
Duling et al. "Mechanical Characterization of Electrospun Polycaprolactone (PCL): A Potential Scaffold for Tissue Engineering" Feb. 2008, J. Biomechanical Engineering 130(1 ):011006-1-011006-13.
Eichaker et al. "Quantification of Tissue-Engineered Trachea Performance with Computational Fluid Dynamics" Aug. 2018, Laryngoscope 128(8):8 Pages.
Engler et al. "Matrix Elasticity Directs Stem Cell Lineage Specification" Aug. 25, 2006, Cell, 126(4):677-689.
Erbel et al. "Aortic Dimensions and the Risk of Dissection" Jan. 2006, Heart 92(1):137-142.
European Search Report and Written Opinion for EP 19894450.6 received Jul. 21, 2022, 9 Pages.
European Supplementary Search Report and Written Opinion for EP 15774154.7 received Sep. 28, 2017, 7 Pages.
Extended European Search Report and Written Opinion for European Application No. 20747880.1, dated Oct. 19, 2022, 19 pages.
Fischer et al. "Organ-Derived Coatings on Electrospun Nanofibers as Ex Vivo Microenvironments" 2011, Biomaterials 32:538-546.
Franklin et al. "Comparison of Platelet-Rich Plasma, Stromal Vascular Fraction (SVF), or SVF with an Injectable PLGA Nanofiber Scaffold for the Treatment of Osteochondral Injury in Dogs" 2017, J. Knee Surgery 31 (7): 12 Pages.
Frey et al. "Electrospinning and Porosity Measurements of Nylon-6/Poly (Ethylene Oxide) Blended Nonwovens" 2007, Journal of Engineered Fibers and Fabrics, 2(1):31-37.
Fujihara et al. "Guided Bone Regeneration Membrane Made of Polycaprolactone/Calcium Carbonate Composite Nano-Fibers" Jul. 2005, Biomaterials 26(19):4139-4147.
Fukunishi et al. "Different Degradation Rates of Nanofiber Vascular Grafts in Small and Large Animal Models" Feb. 2020, Journal of Tissue Engineering and Regenerative Medicine, 14(2):203-214.
Fukunishi et al. "Fast-Degrading Tissue-Engineered Vascular Grafts Lead to Increased Extracellular Matrix Cross-Linking Enzyme Expression" Nov. 2021, Tissue Engineering Part A, 27(21-22):1368-1375.
Fukunishi et al. "Preclinical Study of Patient-Specific Cell-Free Nanofiber Tissue-Engineered Vascular grafts using 3-Dimensional Printing in a Sheep Model" 2016, The Journal of Thoracic and Cardiovascular Surgery, 10 Pages.
Fukunishi et al. "Role of Bone Marrow Mononuclear Cell Seeding for Nanofiber Vascular Grafts" Jan. 2018, Tissue Engineering: Part A, 24(1-2), 10 Pages.
Fukunishi et al. "Tissue-Engineered Small Diameter Arterial Vascular Grafts from Cell-Free Nanofiber PCL/Chitosan Scaffolds in a Sheep Model" Jul. 28, 2016, PLoS One, 11(7):15 Pages, DOI: 10.1371/journal.pone.0158555.
Gaumer et al. "Structure-function Relationships and Source-to-Ground Distance in Electrospun Polycaprolactone" Jun. 2009, Acta Biomaterialia 5(5):1552-1561.
Han et al. "Cell Attachment to Hydrogel-Electrospun Fiber Mat Composite Materials" 2012, J. Functional Biomaterials 3:497-513.
Han et al. "Effects of Hydrophobicity and Mat Thickness on Release from Hydrogel-Electrospun Fiber Mat Composites" 2013, J. Biomaterials Science, Polymer Edition 24(17):2018-2030.
Han et al. "Hydrogel-Electrospun Fiber Composite Materials for Hydrophilic Protein Release" 2012, J. Controlled Release 158:165-170.
Han et al. "Hydrogel-Electrospun Fiber Mat Composite Coatings for Neural Prostheses" Mar. 11, 2011, Frontiers in Neuroengineering 4(2):1-8.
Hashi et al. "Antithrombogenic Modification of Small Diameter Microfibrous Vascular Grafts" Aug. 2010, Arteriosclerosis, Thrombosis and Vascular Biology 30(8):1621-1627.
Hashi et al. "Antithrombogenic Property of Bone Marrow Mesenchymal Stem Cells in Nanofibrous Vascular Grafts" Jul. 17, 2007, Proceedings of the National Academy of Sciences of the United States of America 104 (29):11915-11920.
He et al. "Fabrication of Drug-loaded Electrospun Aligned Fibrous Threads for Suture Applications" Apr. 1, 2009, J. Biomedical Materials Research Part A, US 89(1):80-95, DOI:10.1002/jbm.a. 32004, ISSN 1549-3296, XP055229026.
Heilingoetter et al. "Applications of Electrospinning for Tissue Engineering in Otolaryngology" Apr. 2021, Annals of Otology, Rhinology and Laryngology 130(4):395-404.
Herrera et al. "Randomly Oriented and Aligned Cellulose Fibres Reinforced With Cellulose Nanowhiskers Prepared by Electrospinning" Nov. 12, 2013, Plastic, Rubber and Composites 20(2):57-64.
Horner et al. "Microstructure-Dependent Mechanical Properties of Electrospun Core-Shell Scaffolds at Multi-Scale Levels" Jun. 2016, J. Mechanical Behavior of Biomedical Materials 59:207-219.
Hsu et al. "Nano-sized Beads and Porous Fiber Constructs of Poly(ε-caprolactone) Produced by Electrospinning" 2004, Journal of Material Science, 39(9):3003-3013.
Hsu et al. "N,N-Dimethylformamide Additions to the Solution for the Electrospinning of Poly(ε-caprolactone) Nanofibers" Apr. 2004, Macromolecular Materials and Engineering 289(4):334-340.
Huang et al. "A Review on Polymer Nanofibers by Electrospinning and Their Applications in Nanocomposites" Nov. 2003, Composites Science and Technology 63(15):2223-2253.
Hunsberger et al. "Improving Patient Outcomes with Regenerative Medicine: How Regenerative Medicine Manufacturing Society Plans to Move the Needle Forward in Cell Manufacturing, Standards, 3D Bioprinting, Artificial Intelligence-Enabled Automation, Education, and Training" Jul. 2020, Stem Cells Translational Medicine 9 (7):728-733.
International Search Report and Written Opinion for PCT/US2015/016973 dated May 22, 2015, 9 Pages.
International Search Report and Written Opinion for PCT/US2016/030058 dated Jul. 29, 2016, 10 Pages.
International Search Report and Written Opinion for PCT/US2016/060157 dated Jan. 31, 2017, 8 Pages.
International Search Report and Written Opinion for PCT/US2018/016638 dated Apr. 23, 2018, 11 Pages.
International Search Report and Written Opinion for PCT/US2018/064570 dated Feb. 6, 2019, 9 Pages.
International Search Report and Written Opinion for PCT/US2019/065669 dated Feb. 6, 2020, 11 Pages.

(56) References Cited

OTHER PUBLICATIONS

International Search Report and Written Opinion for PCT/US2021/019043 dated May 4, 2021, 9 Pages.
Johnson et al. "Development of Novel, Bioresorbable, Small-Diameter Electrospun Vascular Grafts" Mar. 2015, J. Tissue Science & Engineering, 6(2):7 Pages.
Johnson et al. "Electrospun PCL in Vitro: A Microstructural Basis for Mechanical Property Changes" 2009, J. Biomaterials Science, Polymer Ed. 20(4):467-481.
Johnson et al. "Microstructure-Property Relationships in a Tissue-Engineering Scaffold" 2007, J. of Applied Polymer Science, 104(5):2919-2927.
Johnson et al. "Quantitative Analysis of Complex Glioma Cell Migration on Electrospun Polycaprolcatone Using Time-Lapse Microscopy" 2009, Tissue Engineering, 15(4):531-540, DOI:10.1089/ten.tec.2008.0486, XP055083103.
Johnson "First-in-the-World Equine Joint Injection for Osteoarthritis" Jul./Aug. 2014, The International Equine Veterinarian, 23-25.
Kang et al. "Plasma Treatment of Textiles—Synthetic Polymer-Based Textiles" Nov. 2004, AATCC Review 4 (11):29-33.
Kannan et al. "Current Status of Prosthetic Bypass Grafts: A Review" 2005, J. Biomedical Materials Research Part B Applied Biomaterials 74B(1):570-581.
Katta et al. "Continuous Electrospinning of Aligned Polymer Nanofibers onto a Wire Drum Collector" Sep. 28, 2004, Nano Letters 4(11):2215-2218, (Abstract Only).
Kazemnejad et al. "Biochemical and Molecular Characterization of Hepatocyte-like Cells Derived From Human Bone Marrow Mesenchymal Stem Cells on a Novel Three-dimensional Biocompatible Nanofibrous Scaffold" Feb. 1, 2009, J. Gastroenterology and Hepatology 24(2):278-287, DOI:10.1111/j.1440-1746.2008.05530.x, ISSN 0815-9319, XP055084180.
Khan et al. "Evaluation of Changes in Morphology and Function of Human Induced Pluripotent Stem Cell Derived Cardiomyocytes (HiPSC-CMs) Cultured on an Aligned-Nanofiber Cardiac Patch" May 19, 2015, PLOS One 10(5):19 Pages, doi:10.1371/journal.pone.0126338, XP055592086.
Khil et al. "Novel Fabricated Matrix via Electrospinning for Tissue Engineering" 2005, J. Biomedical Materials Research Part B: Applied Biomaterials 72B(1):117-124.
Killeen et al. "Rapid Communication: Fully Synthetic Bioengineered Nanomedical Scaffold in Chronic Neuropathic Foot Ulcers" Oct. 2018, Wounds 30(10):E98-E101.
Kim et al. "Controlled Protein Release from Electrospun Biodegradable Fiber Mesh Composed of Poly(ε-caprolactone) and Poly(Ethylene Oxide)" Jun. 29, 2007, International J. Pharmaceutics 338(1-2):276-283.
Kim et al. "Evaluations of Chitosan/Poly(D,L-lactic-co-glycolic acid) Composite Fibrous Scaffold for Tissue Engineering Application" 2013, Macromolecular Research 21:931-939.
Kwon et al. "Electrospun Nano- to Microfiber Fabrics Made of Biodegradable Co Polyesters: Structural Characteristics, Mechanical Properties and Cell Adhesion Potential" Jun. 2005, Biomaterials 26(181):3929-3939.
Lannutti et al. "Electrospinning for Tissue Engineering Scaffolds" Apr. 2007, Materials Science and Engineering C 27(3):504-509.
Lee et al. "Biomedical Applications of Magnetically Functionalized Organic/Inorganic Hybrid Nanofibers" 2015, International J. Molecular Sciences 16:13661-13677.
Lee et al. "Characterization of Nano-Structured poly(ε-caprolactone) Nonwoven Mats via Electrospinning" Feb. 2003, Polymer 44(4):1287-1294.
Lee et al. "Increased Mechanical Properties of Aligned and Isotropic Electrospun PVA Nanofiber Webs by Cellulose Nanowhisker Reinforcement" 2012, Macromolecular Research 20(1):76-83.
Li et al. "A Three-Dimensional Nanofibrous Scaffold for Cartilage Tissue Engineering Using Human Mesenchymal Stem Cells" Feb. 1, 2005, Biomaterials, Elsevier Science Publishers Bv., Barking, GB 26(6):599-609, DOI:10.1016/J.BIOMATERIALS.2004.03.005, ISSN 0142-9612, XP025280436.

Li et al. "Biological Response of Chondrocytes Cultured in Three-Dimensional Nanofibrous Poly(e-Caproiactone) Scaffolds" Dec. 15, 2003, J. Biomedical Materials Research Part A, 67A(4):1105-1114.
Li et al. "Electrospinning Nanofibers as Uniaxially Aligned Arrays and Layer-by-Layer Stacked Films" Feb. 17, 2004, Advanced Materials 16(4):361-366.
Li W-J et al. "Multilineage Differentiation of Human Mesenchymal Stem Cells in a Three-Dimensional Nanofibrous Scaffold" Sep. 2005, Biomaterials 26(25):5158-5166.
Lim et al. "Micropatterning and Characterization of Electrospun Poly(ε-Caprolactone)/Gelatin Nanofiber Tissue Scaffolds by Femtosecond Laser Ablation for Tissue Engineering Applications" Jan. 1, 2011, Biotechnology and Bioengineering, 108(1):116-126.
Liu et al. "Comparison of Different In Vivo Incubation Sites to Produce Tissue-Engineered Small Intestine" Jul. 2018, Tissue Engineering Part A, 24(13-14):1138-1147.
Liu et al. "Electrospun Fibrous Mats on Lithographically Micropatterned Collectors to Control Cellular Behaviors" Nov. 15, 2012, Langmuir 28:17134-17142.
Liu et al. "Enriched Intestinal Stem Cell Seeding Improves the Architecture of Tissue-Engineered Intestine" Aug. 2015, Tissue Engineering: Part C, 21(8):816-824.
Liu et al. "HB-EGF Embedded in PGA/PLLA Scaffolds via Subcritical $CO_2$ Augments the Production of Tissue Engineered Intestine" Oct. 2016, Biomaterials, 103:150-159.
Liu et al. "Modulation of Synthetic Tracheal Grafts with Extracellular Matrix Coatings" Aug. 20, 2021, Bioengineering 8(8):18 Pages(Article No. 116).
Liu et al. "Production of Tissue-Engineered Small Intestine in Rats with Different Ages of Cell Donors" Jun. 2019, Tissue Engineering Part A, 25(11-12), 9 pages.
Liu et al. "Topical Biomaterials to prevent post-Tonsillectomy Hemorrhage" Sep. 6, 2019, J. Otolaryngol Head & Neck Surgery, 48(45):1-17.
Luu et al. "Development of a Nanostructured DNA Delivery Scaffold via Electrospinning of PLGA and PLGA and PLA-PEG Block Copolymers" Apr. 29, 2003, J. of Controlled Release 89(2):341-353.
Macchiarini et al. "Clinical Transplantation of a Tissue-Engineered Airway" Dec. 13, 2008, The Lancet 372 9655):2023-2030.
Maldonado et al. "The Effects of Electrospun Substrate-Mediated Cell Colony Morphology on the Self-Renewal of Human Induced Pluripotent Stem Cells" May 2015, Biomaterials 50:10 Pages.
Manavitehrani et al. "Biomedical Applications of Biodegradable Polyesters," Jan. 16, 2016, Polymers 08 20):1-32.
Martins et al. "Electrospun Nanostructured Scaffolds for Tissue Engineering Applications" 2007, Nanomedicine 2 (6):929-942.
Mathew et al. "Preparation and Anisotropic Mechanical Behavior of Highly-Oriented Electrospun Poly(Butylene terephthalate) Fibers" Aug. 2006, J. Applied Polymer Science 101(3):2017-2021.
Matsushita et al. "Corrugated Nanofiber Tissue-Engineered Vascular Graft to Prevent Kinking for Arteriovenous Shunts in an Ovine Model" Apr. 11, 2020, JVS-Vascular Science 01:100-108.
Matsushita et al. "Novel Reinforcement of Corrugated Nanofiber Tissue-Engineered Vascular Graft to Prevent Aneurysm Formation for Arteriovenous Shunts in an Ovine Model" 2020, JVS-Vascular Science 03:182-191.
McClure et al. "A Three-Layered Electrospun Matrix to Mimic Native Arterial Architecture Using Polycaprolactone, Elastin, and Collagen: A Preliminary Study" 2010, Acta Biomaterialia 6:2422-2433.
Meng et al. "Electrospun Aligned Nanofibers Composite of MWCNT/polyurethane to Enhance Vascular Endothelium Cells Proliferation and Function" Oct. 2010, J. Nanoscience and Nanotechnology 95A(1 ):312-320.
Mori et al. "Fibrocytes Contribute to the Myofibroblast Population in Wounded Skin and Originate from the Bone Narrow" Mar. 10, 2005, Experimental Cell Research 304(1):81-90.
Murthy et al. "Biodegradation of Polymers" 2012, Polymer Science: A Comprehensive Reference 9:547-560.
Nam et al. "Improved Cellular Infiltration in Electrospun Fiber via Engineered Porosity" Sep. 2007, Tissue Engineering 13:(9):2249-2257.

(56) References Cited

OTHER PUBLICATIONS

Nam et al. "Materials Selection and Residual Solvent Retention in Biodegradable Electrospun Fibers" Feb. 5, 2008, J. Applied Polymer Science 107(3): 1547-1554.
Nam et al. "Modulation of Embryonic Mesenchymal Progenitor Cell Differentiation via Control Over Pure Mechanical Modules in Electrospun Nanofibers" Apr. 2011, (Epub Nov. 22, 2010), Acta Biomaterialia 7(4):1516-1524, DOI: 10.1016/j.actbio.2010.11.022.
Nam et al. "Novel Electrospun Scaffolds for the Molecular Analysis of Chondrocytes Under Dynamic Compression" 2009, Tissue Engineering, Part A 15(3):513-523.
Nelson et al. "Media-Based Effects on the Hydrolytic Degradation and Crystallization of Electrospun Synthetic-Biologic Blends" Feb. 2014, J. Materials Science: Materials in Medicine 25(2):297-309.
Niehaus et al. "Comparison of the Mechanical Characteristics of Polymerized Caprolactam and Monofilament Nylon Loops Constructed in Parallel Strands or as Braided Ropes Versus Cranial Cruciate Ligaments of Cattle" Mar. 2013, American J. Veterinary Research 74(03):381-385.
Niehaus et al. "Effects of Orthopedic Implants with a Polycaprolactone Polymer Coating Containing Bone Morphogenetic Protein-2 on Osseointegration in Bones of Sheep" Nov. 2009, American J. Veterinary Research 70(11):1416-1425.
Ong et al. "Bilateral Arteriovenous Shunts as a Method for Evaluating Tissue-Engineered Vascular Grafts in Large Animal Models" Nov. 2017, Tissue Engineering: Part C Methods 23(11):728-735.
Ott et al. "Mechanical Evaluation of Gradient Electrospun Scaffolds with 3D Printed Ring Reinforcements for Tracheal Defect Repair" Apr. 21, 2016, Biomed Materials 11(2):16 Pages.
Pandey et al. "Aligned Nanofiber Material Supports Cell Growth and Increases Osteogenesis in Canine Adipose-Derived Mesenchymal Stem Cells in Vitro" Jul. 2018, J. Biomedical Materials Res A 106(7): 1780-1788.
Park "Lab-Made Organ Implanted for First Time" Jul. 8, 2011, CNN.com Article, 2 Pages, Retrieved from the Internet: http://www.cnn.com/2011/HEALTH/07/07/trachea.transplant/index.html (Jul. 14, 2017).
Pepper et al. "Endoscopic Management of Tissue-Engineered Tracheal Graft Stenosis in an Ovine Model" Oct. 2017, Laryngoscope 127(10):2219-2224.
Pepper et al. "Factors Influencing Poor Outcomes in Synthetic Tissue-Engineered Tracheal Replacement" Sep. 2019, Otolaryngol Head Neck Surgery 161(3):458-467.
Petition for Inter Partes Review of U.S. Pat. No. 10,632,228 (IPR2021-01016), *Nanofiber Solutions, LLC v. Acera Surgical, Inc.*, May 28, 2021, 91 Pages.
Pham et al. "Electrospinning of Polymeric Nanofibers for Tissue Engineering Applications: A Review" 2006, Tissue Engineering 12(5):1197-1211.
Powell et al. "EDC Cross-linking Improves Skin Substitute Strength and Stability" 2006, Biomaterials 27(34): 5821-5827.
Powell et al. "Fiber Density of Electrospun Gelatin Scaffolds Regulates Morphogenesis of Dermal-Epidermal Skin Substitutes" Journal of Biomedical Materials Research, Part A, 2007, 84A(4):1078-1086.
Reneker et al. "Nanometre Diameter Fibres of Polymer, Produced by Electrospinning" 1996, Nanotechnology 7 3):216-223.
Romeo et al. "Rotator Cuff Repair using a Bioresorbable Nanofiber Interposition Scaffold: A Biomechanical and Histologic Analysis in Sheep" Feb. 2022, J. Shoulder and Elbow Surgery, 31(2):402-412.
Roth et al. "Hemoglobin Regulates the Migration of Glioma Cells Along Poly(E-caprolactone)-aligned Nanofibers" Jul. 24, 2014, Sep.-Oct. 2014, AIChE, Biotechnology Progress, 30(5):1214-1220.
Ruoslahti "Brain Extracellular Matrix" 1996, Glycobiology 6(5):489-492.
Samios et al. "In Situ Compatibilization of Polyurethane With Poly(ethylene terephthalate)" 2000, European Polymer J. 36:937-947.

Schneider et al. "Influence of pH on Wound-healing: a New Perspective for Wound-therapy" 2007, Archives of Dermatological Research 298:413-420.
Schwartz et al. "Electrospun Scaffolds Limit the Regenerative Potential of the Airway Epithelium" Aug. 2019, Laryngoscope Investigative Otolaryngology 4(4):446-454.
Shin et al. "Contractile Cardiac Grafts Using a Novel Nanofibrous Mesh" Aug. 2004, Biomaterials 25 17):3717-3723.
Shin et al. "In Vivo Bone Tissue Engineering Using Mesenchymal Stem Cells on a Novel Electrospun Nanofibrous Scaffold" 2004, Tissue Engineering 10(1-2):33-41.
Siallagan et al. "Virtual Surgical Planning, Flow Simulation, and 3-Dimensional Electrospinning of Patient-Specific Grafts to Optimize Fontan Hemodynamics" 2017, Apr. 2018, The J. of Thoracic and Cardiovascular Surgery 155 (4):1-10.
Srikar et al. "Desorption-Limited Mechanism of Release From Polymer Nanofibers" 2008, Langmuir 24(3):965-974.
Stitzel et al. "Controlled Fabrication of a Biological Vascular Substitute" 2006, Biomaterials 27:1088-1094.
Tan et al. "Tracheal Macrophages During Regeneration and Repair of Long-Segment Airway Defects" Apr. 2022, The Laryngoscope 132(4):1737-1746.
Teo et al. "A Review on Electrospinning Design and Nanofibre Assemblies" 2006, Nanotechnology 17(14):R89-R106.
Teo et al. "Electrospun Fibre Bundle Made of Aligned Nanofibers Over Two Fixed Points" Jul. 22, 2005, Nanotechnology 16:1878-1884.
Townsend et al. "Biodegradable Electrospun Patch Containing Cell Adhesion or Antimicrobial Compounds for Trachea Repair in Vivo" Feb. 17, 2020, Biomedical Materials 15(02:025003):13.
Townsend et al. "Reinforced Electrospun Polycaprolactone Nanofibers for Tracheal Repair in an In Vivo Ovine Model" Sep. 2018, Tissue Engineering: Part A24(17-18):1301-1308.
Townsend et al. "Standardization of Microcomputed Tomography for Tracheal Tissue Engineering Analysis" Nov. 2020, Tissue Engineering: Part C 26(11):590-595.
Tse et al. "Current Status of Pipeline Embolization Device in the Treatment of Intracranial Aneurysms: A review" Dec. 2013, World Neurosurgery 80(6):829-835.
Veleva et al. "Interactions between Endothelial Cells and Electrospun Methacrylic Terpolymer Fibers for Engineered Vascular Replacements" Jan. 15, 2009, J. Biomedical Materials Research Part A 91A(4):1131-1139.
Wang et al. "Nanofibres and their Influence on Cells for Tissue Regeneration" 2005, Australian J. Chemistry 58 (10):704-712.
Wiet et al. "Seeding and Implantation of a Biosynthetic Tissue-engineered Tracheal Graft in a Mouse Model" Apr. 2019, J. Visualized Experiments 1(46):1-14.
Xie et al. "Encapsulation of Protein Drugs in Biodegradable Microparticles by Co-axial Electrospray" Jan. 15, 2008, J. Colloid and Interface Science 317(2):469-476.
Yeung et al. "In Vivo Implantation of 3D Printed Customized Branched Tissue Engineered Vascular Graft in Porcine Model" May 2020, The J. Thoracic and Cardiovascular Surgery 159(05):1971-1981.
Yoo et al. "Surface-Functionalized Electrospun Nanofibers for Tissue Engineering and Drug Delivery" Oct. 2009, Advanced Drug Delivery Reviews 61:1033-1042.
Yoshimoto et al. "A Biodegradable Nanofiber Scaffold by Electrospinning and its Potential for Bone Tissue Engineering" May 2003, Biomaterials 24(12):2077-2082.
Yu et al. "Production of Submicrometer Diameter Fibers by Two-Fluid Electrospinning" Sep. 3, 2004, Advanced Materials 16(17):1562-1566.
Zeng et al. "Enzymatic Degradation of Poly(L-lactide) and Poly(ε-Caprolactone) Electrospun Fibers" Dec. 15, 2004, Macromolecular Bioscience 4(12):1118-1125.
Zeng et al. "Ultrafine Fibers Electrospun from Biodegradable Polymers" Jul. 25, 2003, J. Applied Polymer Science 89 4):1085-1092.
Zhang et al. "Electrospinning of Gelatin Fibers and Gelatin/PCL Composite Fibrous Scaffolds" Jan. 2005, J. Biomedical Materials Research Part B: Applied Biomaterials 72B(1):156-165.

(56) References Cited

OTHER PUBLICATIONS

Zhang et al. "Recent Development of Polymer Nanofibers for Biomedical and Biotechnological Applications" 2005, J. Materials Science—Materials in Medicine 6(10):933-946.
Zhu et al. "Characterization of a Co-electrospun Scaffold of HLC/CS/PLA for Vascular Tissue Engineering" 2004, Bio-Medical Material Engineering 24(6):1999-2005.

* cited by examiner

FIG. 3B
FIG. 3A

FIG. 15A
FIG. 15B

METHODS OF TREATING CHRONIC WOUNDS USING ELECTROSPUN FIBERS

CROSS-REFERENCE TO RELATED APPLICATIONS

This application is a continuation of U.S. patent application Ser. No. 16/710,603, filed Dec. 11, 2019, entitled "Methods of Treating Chronic Wounds Using Electrospun Fibers," which claims priority to and benefit of U.S. Provisional Application Ser. No. 62/778,024, filed Dec. 11, 2018, entitled "Methods of Using Electrospun Fibers to Affect the pH of Tissues," which is incorporated herein by reference in its entirety.

BACKGROUND

Chronic wounds present serious health risks to patients, and represent a significant burden on the healthcare system as a whole. These wounds remain a significant healthcare challenge despite extensive research into their underlying physiology and many products developed for their treatment. Because these wounds are so challenging, there remains a need for efficient, effective methods of treating chronic wounds.

SUMMARY

The instant disclosure is directed to methods of treating chronic wounds using electrospun fibers, and methods of affecting the pH of a portion of a body. In some embodiments, a method of treating a chronic wound may comprise applying to the wound a first scaffold comprising an electrospun polymer fiber. The electrospun fiber may comprise a polymer selected from the group consisting of polyglycolic acid, poly(lactide-co-caprolactone), polylactic acid, polycaprolactone, copolymers thereof, and combinations thereof. The first scaffold may have a thickness from about 50 μm to about 1 mm, a length from about 1 cm to about 20 cm, and a width from about 1 cm to about 15 cm. The method may further comprise keeping the first scaffold on the chronic wound for a time period of about 3 days to about 21 days. After the time period passes, the chronic wound may have a decreased planimetric area.

In some embodiments, a method of affecting the initial pH of a portion of a body may comprise applying to the portion of the body a scaffold comprising an electrospun polymer fiber, and allowing at least a portion of the scaffold to degrade, thereby producing a byproduct. The pH of the byproduct may be different from the initial pH of the portion of the body, and producing the byproduct may change the initial pH of the portion of the body.

In an embodiment, a method of reducing the initial pH of a chronic wound may comprise applying to the chronic wound a scaffold comprising an electrospun polymer fiber, and allowing at least a portion of the scaffold to degrade, thereby producing an alpha-hydroxy acid such as lactic acid. The pH of the lactic acid may be lower than the initial pH of the chronic wound, and producing the lactic acid may reduce the initial pH of the chronic wound to a target pH. In certain embodiments, reducing the initial pH of the chronic wound may accelerate or improve healing of the chronic wound.

In an embodiment, there may be provided a scaffold comprising an electrospun polymer fiber for use in a method of affecting the initial pH of a portion of a body, wherein the method comprises applying the scaffold comprising an electrospun polymer fiber to the portion of the body, and allowing at least a portion of the scaffold to degrade, thereby producing a byproduct. The pH of the byproduct may be different from the initial pH of the portion of the body, and producing the byproduct may change the initial pH of the portion of the body.

In an embodiment, there may be provided a scaffold comprising an electrospun polymer fiber for use in a method of reducing the initial pH of a chronic wound, wherein the method comprises applying the scaffold comprising an electrospun polymer fiber to the wound, and allowing at least a portion of the scaffold to degrade, thereby producing a byproduct. The pH of the byproduct may be different from the initial pH of the wound, and producing the byproduct may change the initial pH of the wound. In an embodiment, the byproduct is an alpha-hydroxy acid, or any other acid produced during degradation of an electrospun scaffold, as described herein. In an embodiment, the wound may be a chronic wound.

In an embodiment, there may be provided a scaffold comprising an electrospun polymer fiber for use in a method of accelerating and/or improving healing of a wound, wherein the method comprises applying the scaffold comprising an electrospun polymer fiber to the wound, and allowing at least a portion of the scaffold to degrade, thereby producing a byproduct. The pH of the byproduct may be different from the initial pH of the wound, and producing the byproduct may change the initial pH of the wound. In an embodiment, the byproduct is an alpha-hydroxy acid, or any other acid produced during degradation of an electrospun scaffold, as described herein. In an embodiment, the wound may be a chronic wound. In an embodiment, there is provided a kit comprising two or more scaffolds, each scaffold comprising an electrospun polymer fiber capable of degrading to produce a byproduct, wherein the pH of the byproduct is different from the initial pH of the wound, and wherein the two or more scaffolds are each configured to produce a different byproduct, to degrade at different rates, and/or to produce a different amount of byproduct. Suitably, each scaffold produces a byproduct having a different pH, each being lower than the initial pH of the wound by a different amount. Also included is the kit for use in a method described herein.

BRIEF DESCRIPTION OF THE DRAWINGS

FIG. 3A shows a pressure ulcer on Day 0. An embodiment of a scaffold as described herein was applied to the pressure ulcer on Day 0. FIG. 3B shows the pressure ulcer of FIG. 3A on Day 7. Another embodiment of a scaffold as described herein was applied to the pressure ulcer on Day 7.

4A on Day 32. Another embodiment of a scaffold as described herein was applied to the pressure ulcer on Day 32.

FIG. 15A shows an ulcer on Day 0, at which time an embodiment of a scaffold as described herein was applied. FIG. 15B shows the ulcer of FIG. 15A at Day 13, at which time a third embodiment of a scaffold as described herein was applied.

DETAILED DESCRIPTION

Figure 1:
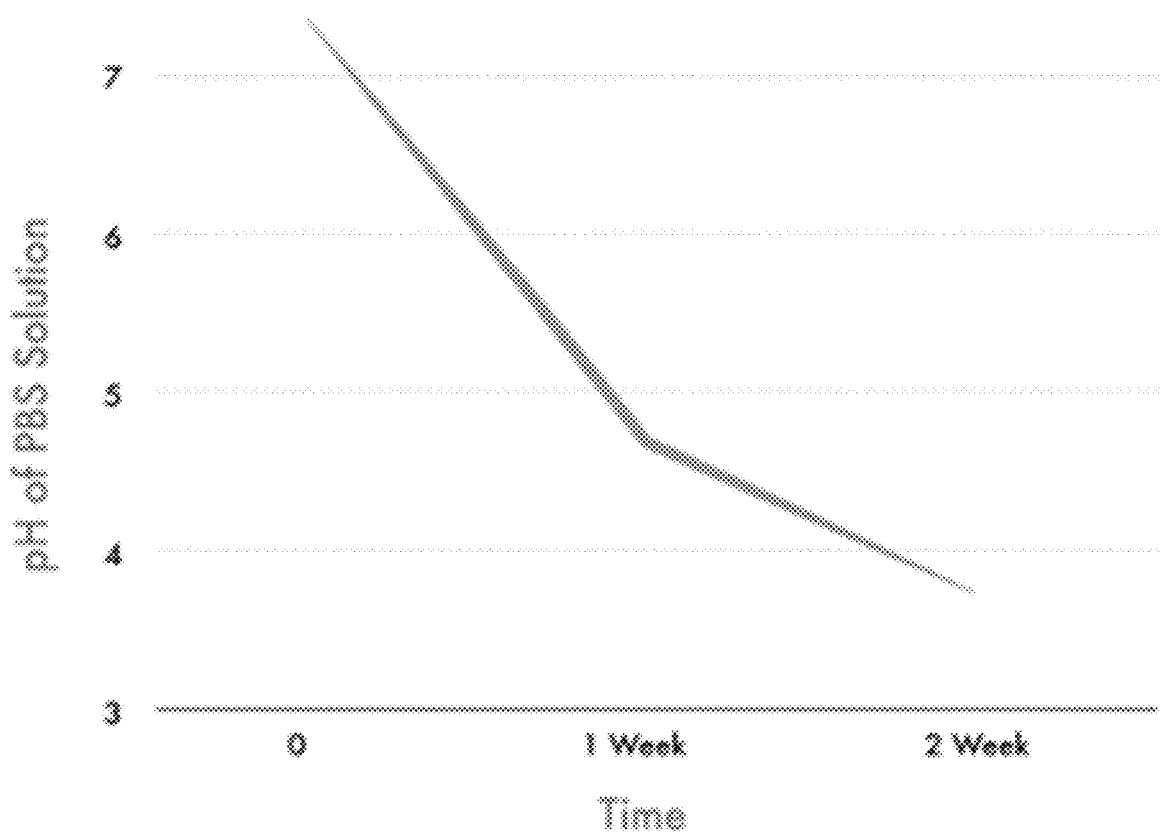
FIG. 1 is a graph showing the effect of the degradation of an embodiment of a scaffold as described herein on the pH of a PBS solution over two weeks.

This disclosure is not limited to the particular systems, devices, and methods described, as these may vary. The terminology used in the description is for the purpose of describing the particular versions or embodiments only, and is not intended to limit the scope of the disclosure.

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a," "an," and "the" include plural references, unless the context clearly dictates otherwise. Thus, for example, reference to a "fiber" is a reference to one or more fibers and equivalents thereof known to those skilled in the art, and so forth.

As used herein, the term "about" means plus or minus 10% of the numerical value of the number with which it is being used. Therefore, about 50 mm means in the range of 45 mm to 55 mm.

As used herein, the term "consists of" or "consisting of" means that the device or method includes only the elements, steps, or ingredients specifically recited in the particular claimed embodiment or claim.

In embodiments or claims where the term comprising is used as the transition phrase, such embodiments can also be envisioned with replacement of the term "comprising" with the terms "consisting of" or "consisting essentially of."

As used herein, the term "improve" is used to convey that the methods of healing tissues as described in embodiments herein change the appearance, form, characteristics and/or the physical or biochemical attributes of the tissues to which they are being provided, applied or administered. Suitably, such changes are beneficial changes, for example in relation to the appearance, form, characteristics and/or the physical or biochemical attributes of the tissues to which the scaffold is applied.

The terms "heal," "treat," "treated," or "treating," as used herein, refers to both therapeutic treatment and prophylactic or preventative measures, wherein the object is to inhibit, prevent or slow down (lessen) an undesired physiological condition, disorder or disease, or to accelerate, improve, inhibit, or otherwise obtain beneficial or desired clinical results. For the purposes of this invention, beneficial or desired clinical results include, but are not limited to, full or partial healing of a wound or damaged tissue; the decrease in size or planimetric area of a wound; decreased inflammation of a wound or damaged tissue; prevention of further wound development or tissue damage; or improvement or alleviation of symptoms, including pain or swelling. Accelerating healing or treating of a wound refers to increasing the rate of onset of a beneficial effect as described above, compared to the rate of onset without use of the scaffold.

By "applying to a wound" is meant any method of contacting the scaffold with all or a portion of a wound. Application may include placing a scaffold on the surface of a wound, and/or implanting a scaffold within a body to make contact with a wound. Suitably, direct contact is made between the scaffold and wound, although it is also envisaged that contact may be indirect, for example where an intervening material, substance or composition is present.

As used herein, the term "subject" includes, but is not limited to, humans, non-human vertebrates, and animals such as wild, domestic, and farm animals. In some embodiments, the term "subject" refers to mammals. In some embodiments, the term "subject" refers to humans. A "tissue" may include any cell or collection of cells within a subject.

As used herein, the terms "wound" and "damaged tissue" may be used interchangeably. A wound or damaged portion of tissue may be located anywhere within a subject's body, either internal or external. A wound or damaged portion of tissue may occur as the result of trauma, surgery, pressure, friction, or a non-traumatic occurrence.

As used herein, the term "chronic wound," which may be used interchangeably herein with the term "non-healing wound," describes a wound or damaged portion of tissue that heals more slowly than a typical wound of the same type. A chronic wound may, for example, fail to heal in the orderly stages in which a typical wound might heal. A chronic wound may also fail to heal within an expected period of time, for a variety of reasons. In other words, a chronic wound is one that may remain in a particular phase of healing for too long, such as the inflammatory phase. One example of a chronic wound is one that does not heal within three months of its development or creation. Chronic wounds may result from factors including pressure, trauma and/or lower extremity wounds, increased bacterial load, excessive proteases, degraded growth factors, matrix metalloproteinases (MMPs), degraded cell surface structures, senescent/aberrant cells and inappropriate treatment. Examples of chronic wounds include ulcers such as venous ulcers, diabetic ulcers, and, pressure ulcers, ischemia, and wounds resulting from radiation poisoning.

Electrospinning Fibers

Electrospinning is a method which may be used to process a polymer solution into a fiber. In embodiments wherein the diameter of the resulting fiber is on the nanometer scale, the fiber may be referred to as a nanofiber. Fibers may be formed into a variety of shapes by using a range of receiving surfaces, such as mandrels or collectors. In some embodiments, a flat shape, such as a sheet or sheet-like fiber mold, a fiber scaffold and/or tube, or a tubular lattice, may be formed by using a substantially round or cylindrical mandrel. In certain embodiments, the electrospun fibers may be cut and/or unrolled from the mandrel as a fiber mold to form the sheet. The resulting fiber molds or shapes may be used in many applications, including filters and the like.

Electrospinning methods may involve spinning a fiber from a polymer solution by applying a high DC voltage potential between a polymer injection system and a mandrel. In some embodiments, one or more charges may be applied to one or more components of an electrospinning system. In some embodiments, a charge may be applied to the mandrel, the polymer injection system, or combinations or portions thereof. Without wishing to be bound by theory, as the polymer solution is ejected from the polymer injection system, it is thought to be destabilized due to its exposure to a charge. The destabilized solution may then be attracted to a charged mandrel. As the destabilized solution moves from the polymer injection system to the mandrel, its solvents may evaporate and the polymer may stretch, leaving a long, thin fiber that is deposited onto the mandrel. The polymer solution may form a Taylor cone as it is ejected from the polymer injection system and exposed to a charge.

In certain embodiments, a first polymer solution comprising a first polymer and a second polymer solution comprising a second polymer may each be used in a separate polymer injection system at substantially the same time to produce one or more electrospun fibers comprising the first polymer interspersed with one or more electrospun fibers comprising the second polymer. Such a process may be referred to as "co-spinning" or "co-electrospinning," and a scaffold produced by such a process may be described as a co-spun or co-electrospun scaffold. Therefore, a co-spun or co-electrospun scaffold as referred to herein may comprise one or more electrospun fibers comprising a first polymer interspersed with one or more electrospun fibers comprising a second polymer. The first and second polymers may be as described herein.

Polymer Injection System

A polymer injection system may include any system configured to eject some amount of a polymer solution into an atmosphere to permit the flow of the polymer solution from the injection system to the mandrel. In some embodiments, the polymer injection system may deliver a continuous or linear stream with a controlled volumetric flow rate of a polymer solution to be formed into a fiber. In some embodiments, the polymer injection system may deliver a variable stream of a polymer solution to be formed into a fiber. In some embodiments, the polymer injection system may be configured to deliver intermittent streams of a polymer solution to be formed into multiple fibers. In some embodiments, the polymer injection system may include a syringe under manual or automated control. In some embodiments, the polymer injection system may include multiple syringes and multiple needles or needle-like components under individual or combined manual or automated control. In some embodiments, a multi-syringe polymer injection system may include multiple syringes and multiple needles or needle-like components, with each syringe containing the same polymer solution. In some embodiments, a multi-syringe polymer injection system may include multiple syringes and multiple needles or needle-like components, with each syringe containing a different polymer solution. In some embodiments, a charge may be applied to the polymer injection system, or to a portion thereof. In some embodiments, a charge may be applied to a needle or needle-like component of the polymer injection system.

In some embodiments, the polymer solution may be ejected from the polymer injection system at a flow rate of less than or equal to about 5 mL/h per needle. In other embodiments, the polymer solution may be ejected from the polymer injection system at a flow rate per needle in a range from about 0.01 mL/h to about 50 mL/h. The flow rate at which the polymer solution is ejected from the polymer injection system per needle may be, in some non-limiting examples, about 0.01 mL/h, about 0.05 mL/h, about 0.1 mL/h, about 0.5 mL/h, about 1 mL/h, about 2 mL/h, about 3 mL/h, about 4 mL/h, about 5 mL/h, about 6 mL/h, about 7 mL/h, about 8 mL/h, about 9 mL/h, about 10 mL/h, about 11 mL/h, about 12 mL/h, about 13 mL/h, about 14 mL/h, about 15 mL/h, about 16 mL/h, about 17 mL/h, about 18 mL/h, about 19 mL/h, about 20 mL/h, about 21 mL/h, about 22 mL/h, about 23 mL/h, about 24 mL/h, about 25 mL/h, about 26 mL/h, about 27 mL/h, about 28 mL/h, about 29 mL/h, about 30 mL/h, about 31 mL/h, about 32 mL/h, about 33 mL/h, about 34 mL/h, about 35 mL/h, about 36 mL/h, about 37 mL/h, about 38 mL/h, about 39 mL/h, about 40 mL/h, about 41 mL/h, about 42 mL/h, about 43 mL/h, about 44 mL/h, about 45 mL/h, about 46 mL/h, about 47 mL/h, about 48 mL/h, about 49 mL/h, about 50 mL/h, or any range between any two of these values, including endpoints.

As the polymer solution travels from the polymer injection system toward the mandrel, the diameter of the resulting fibers may be in the range of about 100 nm to about 1500 nm. Some non-limiting examples of electrospun fiber diameters may include about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1,000 nm, about 1,050 nm, about 1,100 nm, about 1,150 nm, about 1,200 nm, about 1,250 nm, about 1,300 nm, about 1,350 nm, about 1,400 nm, about 1,450 nm, about 1,500 nm, or any range between any two of these values, including endpoints. In some embodiments, the electrospun fiber diameter may be from about 300 nm to about 1300 nm. In an embodiment, the electrospun fiber diameter may be about 1 μm, about 2 μm, about 3 μm, about 4 μm, about 5 μm, about 6 μm, about 7 μm, about 8 μm, about 9 μm, about 10 μm, or any range between any two of these values, including endpoints.

Polymer Solution

In some embodiments, the polymer injection system may be filled with a polymer solution. In some embodiments, the polymer solution may comprise one or more polymers. In some embodiments, the polymer solution may be a fluid formed into a polymer liquid by the application of heat. A polymer solution or the resulting electrospun polymer fibers may include, for example, non-resorbable polymers, resorbable polymers, natural polymers, or a combination thereof.

In some embodiments, the polymers may include, for example, nylon, nylon 6,6, polycaprolactone, polyethylene oxide terephthalate, polybutylene terephthalate, polyethylene oxide terephthalate-co-polybutylene terephthalate, polyethylene terephthalate, polyurethane, polyethylene, polyethylene oxide, polyvinylpyrrolidone, polyester, polymethylmethacrylate, polyacrylonitrile, silicone, polycarbonate, polylactide, polyglycolide, polyether ketone ketone, polyether ether ketone, polyether imide, polyamide, polystyrene, polyether sulfone, polysulfone, polyvinyl acetate, polytetrafluoroethylene, polyvinylidene fluoride, polylactic acid, polyglycolic acid, polylactide-co-glycolide, poly(lactide-co-caprolactone), polyglycerol sebacate, polydioxanone, polyhydroxybutyrate, poly-4-hydroxybutyrate, trimethylene carbonate, polydiols, polyesters, collagen, gelatin, fibrin, fibronectin, albumin, hyaluronic acid, elastin, chitosan, alginate, silk, copolymers thereof, and combinations thereof. In an embodiment, a combination of polymers may include polymers selected from polylactic acid, polyglycolic acid, polylactide-co-glycolide, and poly(lactide-co-caprolactone). In an embodiment, a combination of polymers may comprise polyglycolic acid and poly(lactide-co-caprolactone).

It may be understood that polymer solutions or the resulting electrospun polymer fibers may also include a combination of one or more of non-resorbable, resorbable polymers, and naturally occurring polymers in any combination or compositional ratio. In an alternative embodiment, the polymer solutions or the resulting electrospun polymer fibers may include a combination of two or more non-resorbable polymers, two or more resorbable polymers or two or more naturally occurring polymers. In some non-limiting examples, the polymer solution or the resulting electrospun polymer fibers may comprise a weight percent ratio of, for example, from about 5% to about 90%. Non-limiting examples of such weight percent ratios may include about 5%, about 10%, about 15%, about 20%, about 25%, about 30%, about 33%, about 35%, about 40%, about 45%, about 50%, about 55%, about 60%, about 66%, about 70%, about 75%, about 80%, about 85%, about 90%, or ranges between any two of these values, including endpoints.

In some embodiments, the polymer solution may comprise one or more solvents. In some embodiments, the solvent may comprise, for example, polyvinylpyrrolidone, hexafluoro-2-propanol (HFIP), acetone, dimethylformamide, dimethylsulfoxide, N-methylpyrrolidone, N,N-dimethylformamide, Nacetonitrile, hexanes, ether, dioxane, ethyl acetate, pyridine, toluene, xylene, tetrahydrofuran, trifluoroacetic acid, hexafluoroisopropanol, acetic acid, dimethylacetamide, chloroform, dichloromethane, water, alcohols, ionic compounds, or combinations thereof. The concentration range of polymer or polymers in solvent or solvents may be, without limitation, from about 1 wt % to about 50 wt %. Some non-limiting examples of polymer concentration in solution may include about 1 wt %, 3 wt %, 5 wt %, about 10 wt %, about 15 wt %, about 20 wt %, about 25 wt %, about 30 wt %, about 35 wt %, about 40 wt %, about 45 wt %, about 50 wt %, or ranges between any two of these values, including endpoints.

In some embodiments, the polymer solution or the resulting electrospun polymer fibers may also include additional materials. Non-limiting examples of such additional materials may include radiation opaque materials, contrast agents, electrically conductive materials, fluorescent materials, luminescent materials, antibiotics, growth factors, vitamins, cytokines, steroids, anti-inflammatory drugs, small molecules, sugars, salts, peptides, proteins, cell factors, DNA, RNA, other materials to aid in non-invasive imaging, or any combination thereof. In some embodiments, the radiation opaque materials may include, for example, barium, tantalum, tungsten, iodine, gadolinium, gold, platinum, bismuth, or bismuth (III) oxide. In some embodiments, the electrically conductive materials may include, for example, gold, silver, iron, or polyaniline.

In certain embodiments, the polymer solution or the resulting electrospun polymer fibers may comprise an agent. The agent may be, for example, any agent that comprises a compound for affecting cellular changes in a tissue. In some embodiments, the agent may be a pharmaceutical. In certain embodiments, the agent may be, for example, an anti-proliferative compound, a vasodilator, a vasoconstrictor, an analgesic, or any combination thereof. In some embodiments, the agent may comprise an anti-proliferative compound selected from paclitaxel, sirolimus, or any combination thereof. In other embodiments, the agent may be selected from miRNA, a gene vector, a peptide, a stem cell, a protein, a ligand, a lipid, or any combination thereof.

In some embodiments, the additional materials and/or agents may be present in the polymer solution or in the resulting electrospun polymer fibers in an amount from about 1 wt % to about 1500 wt % of the polymer mass. In some non-limiting examples, the additional materials may be present in the polymer solution or in the resulting electrospun polymer fibers in an amount of about 1 wt %, about 5 wt %, about 10 wt %, about 15 wt %, about 20 wt %, about 25 wt %, about 30 wt %, about 35 wt %, about 40 wt %, about 45 wt %, about 50 wt %, about 55 wt %, about 60 wt %, about 65 wt %, about 70 wt %, about 75 wt %, about 80 wt %, about 85 wt %, about 90 wt %, about 95 wt %, about 100 wt %, about 125 wt %, about 150 wt %, about 175 wt %, about 200 wt %, about 225 wt %, about 250 wt %, about 275 wt %, about 300 wt %, about 325 wt %, about 350 wt %, about 375 wt %, about 400 wt %, about 425 wt %, about 450 wt %, about 475 wt %, about 500 wt %, about 525 wt %, about 550 wt %, about 575 wt %, about 600 wt %, about 625 wt %, about 650 wt %, about 675 wt %, about 700 wt %, about 725 wt %, about 750 wt %, about 775 wt %, about 800 wt %, about 825 wt %, about 850 wt %, about 875 wt %, about 900 wt %, about 925 wt %, about 950 wt %, about 975 wt %, about 1000 wt %, about 1025 wt %, about 1050 wt %, about 1075 wt %, about 1100 wt %, about 1125 wt %, about 1150 wt %, about 1175 wt %, about 1200 wt %, about 1225 wt %, about 1250 wt %, about 1275 wt %, about 1300 wt %, about 1325 wt %, about 1350 wt %, about 1375 wt %, about 1400 wt %, about 1425 wt %, about 1450 wt %, about 1475 wt %, about 1500 wt %, or any range between any of these two values, including endpoints.

The type of polymer in the polymer solution may determine the characteristics of the electrospun fiber. Some fibers may be composed of polymers that are bio-stable and not absorbable or biodegradable when implanted. Such fibers may remain generally chemically unchanged for the length of time in which they remain implanted. Alternatively, fibers may be composed of polymers that may be absorbed or bio-degraded over time, slowly, rapidly, or at any rate in between slowly and rapidly. It may be further understood that a polymer solution and its resulting electrospun fiber(s) may be composed or more than one type of polymer, and that each polymer therein may have a specific characteristic, such as bio-stability, biodegradability, or bioabsorbability. Suitably, in the scaffolds of the present invention at least one type of fiber is biodegradable or absorbed when implanted or applied to a wound. In a suitable embodiment, more than one type of fiber in a scaffold is biodegradable or absorbed when implanted or applied to a wound. In a suitable embodiment, the scaffold may be composed entirely of fibers which are biodegradable or absorbed when implanted or applied to a wound.

Applying Charges to Electrospinning Components

In an electrospinning system, one or more charges may be applied to one or more components, or portions of components, such as, for example, a mandrel or a polymer injection system, or portions thereof. In some embodiments, a positive charge may be applied to the polymer injection system, or portions thereof. In some embodiments, a negative charge may be applied to the polymer injection system, or portions thereof. In some embodiments, the polymer injection system, or portions thereof, may be grounded. In some embodiments, a positive charge may be applied to mandrel, or portions thereof. In some embodiments, a negative charge may be applied to the mandrel, or portions thereof. In some embodiments, the mandrel, or portions thereof, may be grounded. In some embodiments, one or more components or portions thereof may receive the same charge. In some embodiments, one or more components, or portions thereof, may receive one or more different charges.

The charge applied to any component of the electrospinning system, or portions thereof, may be from about −15 kV to about 30 kV, including endpoints. In some non-limiting examples, the charge applied to any component of the electrospinning system, or portions thereof, may be about −15 kV, about −10 kV, about −5 kV, about −4 kV, about −3 kV, about −1 kV, about −0.01 kV, about 0.01 kV, about 1 kV, about 5 kV, about 10 kV, about 11 kV, about 11.1 kV, about 12 kV, about 15 kV, about 20 kV, about 25 kV, about 30 kV, or any range between any two of these values, including endpoints. In some embodiments, any component of the electrospinning system, or portions thereof, may be grounded.

Mandrel Movement During Electrospinning

During electrospinning, in some embodiments, the mandrel may move with respect to the polymer injection system. In some embodiments, the polymer injection system may move with respect to the mandrel. The movement of one electrospinning component with respect to another electrospinning component may be, for example, substantially rotational, substantially translational, or any combination thereof. In some embodiments, one or more components of the electrospinning system may move under manual control. In some embodiments, one or more components of the electrospinning system may move under automated control. In some embodiments, the mandrel may be in contact with or mounted upon a support structure that may be moved using one or more motors or motion control systems. The pattern of the electrospun fiber deposited on the mandrel may depend upon the one or more motions of the mandrel with respect to the polymer injection system. In some embodiments, the mandrel surface may be configured to rotate about its long axis. In one non-limiting example, a mandrel having a rotation rate about its long axis that is faster than a translation rate along a linear axis, may result in a nearly helical deposition of an electrospun fiber, forming windings about the mandrel. In another example, a mandrel having a translation rate along a linear axis that is faster than a rotation rate about a rotational axis, may result in a roughly linear deposition of an electrospun fiber along a liner extent of the mandrel.

Methods of Treating Chronic Wounds Using Electrospun Fibers

The instant disclosure is directed to methods of treating chronic wounds using electrospun fibers. It may be understood that the devices and methods described herein may be applied to any medical procedure, and that the examples described herein are non-limiting.

Methods of treating chronic wounds may employ electrospun fibers, as described herein. In some embodiments, a method of treating a chronic wound may comprise applying to the chronic wound a scaffold comprising an electrospun fiber, as described herein. In certain embodiments, the electrospun fiber may comprise polyglycolic acid, poly(lactide-co-caprolactone), polylactic acid, polycaprolactone, copolymers thereof, or combinations thereof. In one embodiment, the electrospun polymer comprises a first fiber comprising polyglycolic acid and a second fiber comprising poly(lactide-co-caprolactone), wherein the first fiber and the second fiber are co-spun, as described herein.

In certain embodiments, the scaffold may have a thickness from about 50 μm to about 1 mm. The thickness of the scaffold may be, for example, about 50 μm, about 60 μm, about 70 μm, about 80 μm, about 90 μm, about 100 μm, about 150 μm, about 200 μm, about 250 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm, about 1 mm, or any range between any two of these values, including endpoints.

In some embodiments, the scaffold may have a length from about 1 cm to about 20 cm. The length of the scaffold may be, for example, about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, or any range between any two of these values, including endpoints.

In some embodiments, the scaffold may have a width from about 1 cm to about 20 cm. The width of the scaffold may be, for example, about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, or any range between any two of these values, including endpoints.

The method of treating the chronic wound may further comprise keeping the first scaffold on the chronic wound for a time period. In some embodiments, the time period may be from about 3 days to about 21 days. The time period may be, for example, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, or any range between any two of these values, including endpoints.

In certain embodiments, after the time period has passed, the chronic wound will have a decreased planimetric area. The decrease in the planimetric area of the chronic wound will correspond to the treatment of the chronic wound. The chronic wound may have, for example, a decrease in planimetric area of about 1% to about 100%. The decrease in planimetric area may be, for example, about 1%, about 5%, about 10%, about 20%, about 30%, about 40%, about 50%, about 60%, about 70%, about 80%, about 90%, about 100%, or any range between any two of these values, including endpoints.

In some embodiments, the method may further comprise applying a second scaffold, as described herein, to the chronic wound. The method may also comprise keeping the second scaffold on the chronic wound for a second time period, as described herein. After the second time period, the chronic wound may have a decreased planimetric area.

In certain embodiments, the step of applying another scaffold, as described herein, may be repeated with a third scaffold, a fourth scaffold, a fifth scaffold, a sixth scaffold, and so on. In some embodiments, the method may also comprise trimming or shaping the scaffold to fit the chronic wound, or using multiple scaffolds to cover a single chronic wound.

Methods of Using Electrospun Fibers to Affect the pH of Tissues

Without wishing to be bound by theory, wounded or damaged tissue may have a pH that is different from healthy, intact tissue. Chronic skin wounds, for example, frequently have an alkaline pH in the range of about 7.0 to about 9.0. Healthy skin, on the other hand, typically has a slightly acidic pH in the range of about 4.0 to about 6.0. Furthermore, the pH of a typical wound gradually decreases as the wound heals. Reducing the pH of a wound or damaged tissue, therefore, may improve and/or accelerate the healing of a wound. Reducing the pH of a wound or damaged tissue, however, must be done carefully and in a controlled manner. Therefore, there exists a need for methods to properly affect, and in some cases reduce, the pH of tissues so as to augment their healing. Without wishing to be bound by theory, scaffolds comprising electrospun polymer fibers may be appropriate for these methods, because the fibers degrade at controlled and predictable rates, and particular polymers may degrade to produce acidic byproducts such as lactic acid. Other acidic byproducts may include an alpha-hydroxy acid such as lactic acid, glycolic acid, caproic acid, lactate, derivatives thereof, and combinations thereof. These benefits may be augmented by other benefits of scaffold use, such as increased cell and growth factor retention.

Without wishing to be bound by theory, reducing the pH of a given tissue, wound, or damaged area using such scaffolds may have a number of beneficial effects. Such a process may, for example, increase collagen deposition within the target area, increase or promote angiogenesis, increase endothelial progenitor cell recruitment, increase the presence of potent growth factors (e.g., VEGF, TGF-$\beta$, interleukins, and the like), increase local partial oxygen pressure, increase available oxygen via the Bohr effect, reduce the toxicity of bacterial enzymes and metabolites, enhance the destruction of abnormal collagen, increase macrophage and fibroblast activity, and improve immunity to infection. Therefore, the present invention also relates to a method for increasing collagen deposition within a target area, a method for increasing or promote angiogenesis, a method for increasing endothelial progenitor cell recruitment, a method for increasing the presence of potent growth factors (e.g., VEGF, TGF-$\beta$, interleukins, and the like), a method for increasing local partial oxygen pressure, a method for increasing available oxygen via the Bohr effect in a target area, a method for reducing the toxicity of bacterial enzymes and metabolites, a method for enhancing the destruction of abnormal collagen, a method for increasing macrophage and fibroblast activity, and/or a method for improve immunity to infection, wherein the method comprises applying to the portion of the body a scaffold comprising an electrospun polymer fiber, and allowing at least a portion of the scaffold to degrade, thereby producing a byproduct. The pH of the byproduct may be different from the initial pH of the portion of the body, and producing the byproduct may change the initial pH of the portion of the body. The method may be as described herein. Also provided is a scaffold as described herein for use in any one or more of the above described methods. The scaffold may be as described herein.

Accordingly, such scaffolds may be used to affect the pH of tissues within a portion of a body. Such methods may be used to alter the "initial pH" of a tissue within a portion of a body—that is, the pH of the tissue before the methods described herein are performed. Herein, "affecting" the pH includes altering the initial pH of a tissue within a portion of the body, suitably reducing the pH of a tissue within a portion of the body. The pH may be affected for at least as long as the scaffold remains in contact with the tissue. In some embodiments, a method of affecting the initial pH of the portion of the body may comprise applying to the portion of the body a scaffold comprising an electrospun polymer fiber, as described herein. In an embodiment, the portion of the body may comprise a wound, a tissue, or any combination thereof. In certain embodiments, the portion of the body may comprise a chronic wound.

In some embodiments, the electrospun polymer fiber may comprise any polymer described herein. In certain embodiments, the electrospun polymer fiber may comprise any polymer that produces an acidic byproduct during degradation. In some embodiments, the electrospun polymer fiber may comprise, for example, polyglycolic acid, poly(lactide-co-caprolactone), polylactic acid, polycaprolactone, copolymers thereof, or combinations thereof. In an embodiment, the electrospun polymer fiber may comprise a first fiber and a second fiber, wherein the first fiber and the second fiber are co-spun. In certain embodiments, the first fiber may comprise polyglycolic acid and the second fiber may comprise poly(lactide-co-caprolactone). Without wishing to be bound by theory, such an embodiment may be particularly beneficial because its bi-component nature may combine quickly degrading fibers (for a rapid initial release of a byproduct) and more slowly degrading fibers (for a sustained release of a byproduct).

A scaffold as described herein may adopt any suitable form. For example, a scaffold may be in the form of a textile, as an electrospun or otherwise fabricated material comprising fibers. The scaffold may be a mesh structure, comprising pores, pockets, voids, holes, spaces etc. Alternatively, the scaffold may be an unmeshed structure, such as a block polymer, polymer sheet or formed polymer scaffold. A scaffold may comprise a combination of a mesh and unmeshed structure. The scaffold may be of any suitable size and shape configured to fit in or around a particular tissue, for example a flat shape, such as a sheet or sheet-like fiber mold, a fiber scaffold and/or tube, or a tubular lattice. The scaffold may have a rigid shape or a flexible shape which molds or forms to the portion of the body to which it is applied. The fibers may be continuous, or shorter fragments. They may be substantially parallel, randomly aligned, or in a defined configuration such as hatched. Fragments of fibers may form aggregates (clusters), which may have a range of shapes including spherical, ellipsoidal, globular, and flattened cylinder shapes.

In some embodiments, the method of affecting the initial pH of the portion of the body may further comprise allowing at least a portion of the scaffold to degrade, thereby producing a byproduct. Without wishing to be bound by theory, the degradation may occur simply by placing the scaffold in physical communication with a portion of the body. This portion may comprise a wound, or may comprise tissue adjacent to a wound In certain embodiments, the byproduct may be an acidic byproduct. In an embodiment, the byproduct may be a byproduct that a mammalian cell will convert to lactate. The byproduct may include, for example, an alpha-hydroxy acid such as lactic acid, glycolic acid, caproic acid, lactate, derivatives thereof, and combinations thereof. In some embodiments, the byproduct may have a pH from about 3.0 to about 4.0. The byproduct may have a pH of, for example, about 3.0, about 3.1, about 3.2, about 3.3, about 3.4, about 3.5, about 3.6, about 3.7, about 3.8, about 3.9, about 4.0, or any range between any two of these values, including endpoints.

In some embodiments, the pH of the byproduct may be different from the initial pH of the portion of the body. In certain embodiments, the pH of the byproduct may be lower than the initial pH of the portion of the body, while in other embodiments, the pH of the byproduct may be higher than the initial pH of the portion of the body. In certain embodiments, the byproduct may be an acidic byproduct. In some embodiments, the byproduct may be one or more alpha-hydroxy acids. In one example, the byproduct may comprise lactic acid, which has a pH of about 3.5. In some embodiments the initial pH of the portion of the body may be, for example, from about 7.0 to about 9.0. In such an example, the pH of the byproduct (lactic acid; pH about 3.5) would be lower than the initial pH of the portion of the body (about 7.0 to about 9.0). The pH of the portion of the body may be, for example, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, or any range between any two of these values, including endpoints.

In some embodiments, producing the byproduct may change the initial pH of the portion of the body. That is, in some examples, the production of the byproduct in physical communication with the portion of the body may change the pH of the portion of the body simply by its proximity. In some embodiments, producing the byproduct may change the initial pH of the portion of the body to a target pH of the portion of the body. The change in pH may be an increase, or it may be a decrease. In certain examples, the target pH for the portion of the body may be any pH that is normal, average, or typical, for that portion of the body when it is healthy and intact. In some embodiments, the target pH may be from about 4.0 to about 6.0. The target pH may be, for example, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, or any range between any two of these values, including endpoints.

In some embodiments, the target pH may be reached by the steps of the methods described herein over a period of time. In certain embodiments, the period of time in which the target pH may be reached may be from about 1 hour to about 24 hours. The period of time may be, for example, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or any range between any two of these values, including endpoints.

In some embodiments, the step of allowing at least the portion of the scaffold to degrade may be done over a period of time. In certain embodiments, the period of time over which the portion of the scaffold may be allowed to degrade may be from about 1 hour to about 14 days. The period of time may be, for example, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 8 days, about 9 days, about 10 days, about 11 days, about 12 days, about 13 days, about 14 days, or any range between any two of these values, including endpoints. Quickly degrading fibers as referred to herein may degrade within a period of time from about 1 hour to about 3 days. The time period may be, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, or any range between any two of these values, including endpoints. Slowly degrading fibers as referred to herein may degrade within a period of time from about 3 days to 7 days or longer for example up to 14 days, or any range between any two of these values, including endpoints.

In an embodiment, a method of reducing the initial pH of a chronic wound may comprise applying to the chronic wound a scaffold comprising an electrospun polymer fiber, as described herein. In some embodiments, the method may further comprise allowing at least a portion of the scaffold to degrade as described herein, thereby producing a byproduct, suitably an acidic byproduct as described herein, including an alpha-hydroxy acid such as lactic acid. In an embodiment, the pH of the lactic acid may be lower than the initial pH of the chronic wound, as described herein. In some embodiments, producing the acidic byproduct such as lactic acid may reduce the initial pH of the chronic wound to a target pH, as described herein.

In an embodiment, for example, the initial pH of the chronic wound may be from about 7.0 to about 9.0, as described herein. In some embodiments, for example, the target pH may be from about 4.0 to about 6.0, as described herein. In some embodiments, performing the method of reducing the initial pH of the chronic wound may accelerate, augment, or improve healing of the chronic wound, as described herein.

In an embodiment, a method of reducing the initial pH of a chronic wound may comprise applying to the chronic wound a scaffold comprising an electrospun polymer fiber, and allowing at least a portion of the scaffold to degrade, thereby producing an acidic byproduct as described herein, including an alpha-hydroxy acid such as lactic acid. The pH of the alpha-hydroxy acid may be lower than the initial pH of the chronic wound, and producing the alpha-hydroxy acid may reduce the initial pH of the chronic wound to a target pH of about 4.0, about 5.0, or about 6.0. In certain embodiments, reducing the initial pH of the chronic wound may accelerate or improve healing of the chronic wound. Suitably, the electrospun polymer fiber may comprise, for example, polyglycolic acid, poly(lactide-co-caprolactone), polylactic acid, polycaprolactone, copolymers thereof, or combinations thereof. Suitably, an electrospun polymer fiber may comprise polyglycolic acid and/or poly(lactide-co-caprolactone). Suitably, a first polymer fiber may comprise polyglycolic acid and a second polymer fiber may comprise poly(lactide-co-caprolactone). Suitably, the acidic by product is an alpha-hydroxy acid such as lactic acid. The diameter of the fibers may be in the range from about 1 μm to about 100 μm. Suitably, the diameter of the fibers may be from about 1 μm to about 5 μm. Suitably, a first electrospun fiber may degrade within 1 hour to 3 days, and a second electrospun fiber may degrade from 3 days to 7 days or longer. Suitably, the scaffold may be configured to provide a reduction in pH to a target pH in about 1 hour about 2 hours, about 3 hours, about 4 hours, about 8 hours, about 12 hours, about 16 hours, about 20 hours, or about 24 hours. Suitably, the wound may be an ulcer.

In an embodiment, there may be provided a scaffold comprising an electrospun polymer fiber for use in a method of affecting the initial pH of a portion of a body, wherein the method comprises applying to the portion of the body the scaffold comprising an electrospun polymer fiber, and allowing at least a portion of the scaffold to degrade, thereby producing a byproduct. The pH of the byproduct may be different from the initial pH of the portion of the body, and producing the byproduct may change the initial pH of the portion of the body. Suitably, the electrospun polymer fiber may comprise, for example, polyglycolic acid, poly(lactide-co-caprolactone), polylactic acid, polycaprolactone, copolymers thereof, or combinations thereof. Suitably, an electrospun polymer fiber may comprise polyglycolic acid and/or poly(lactide-co-caprolactone). Suitably, a first polymer fiber may comprise polyglycolic acid and a second polymer fiber may comprise poly(lactide-co-caprolactone). Suitably, the acidic by product is an alpha-hydroxy acid such as lactic acid. The diameter of the fibers may be in the range from about 1 μm to about 100 μm. In certain embodiments, the diameter of the fibers may be in the range from about 1 μm to about 5 μm. Suitably, a first electrospun fiber may degrade within 1 hour to 3 days, and a second electrospun fiber may degrade from 3 days to 7 days or longer. Suitably, the scaffold may be configured to provide a reduction in pH to a target pH in about 1 hour about 2 hours, about 3 hours, about 4 hours, about 8 hours, about 12 hours, about 16 hours, about 20 hours, or about 24 hours. Suitably, the wound may be an ulcer.

In an embodiment, there may be provided a scaffold comprising an electrospun polymer fiber for use in a method of reducing the initial pH of a chronic wound, wherein the method comprises applying to the wound the scaffold, and allowing at least a portion of the scaffold to degrade, thereby producing a byproduct. The pH of the byproduct may be different from the initial pH of the wound, and producing the byproduct may change the initial pH of the wound. In some embodiments, the byproduct may be an acidic byproduct. In certain embodiments, the byproduct may be an alpha-hydroxy acid. In an embodiment, the byproduct is lactic acid, or any other acid produced during degradation of an electrospun scaffold, as described herein. In an embodiment, the wound may be a chronic wound. Suitably, the electrospun polymer fiber may comprise, for example, polyglycolic acid, poly(lactide-co-caprolactone), polylactic acid, polycaprolactone, copolymers thereof, or combinations thereof. Suitably, an electrospun polymer fiber may comprise polyglycolic acid and/or poly(lactide-co-caprolactone). Suitably, a first polymer fiber may comprise polyglycolic acid and a second polymer fiber may comprise poly(lactide-co-caprolactone). Suitably, the acidic by product is an alpha-hydroxy acid such as lactic acid. The diameter of the fibers may be in the range from about 1 μm to about 100 μm. In certain embodiments, the diameter of the fibers may be in the range from about 1 μm to about 5 μm. Suitably, a first electrospun fiber may degrade within 1 hour to 3 days, and a second electrospun fiber may degrade from 3 days to 7 days or longer. Suitably, the scaffold may be configured to provide a reduction in pH to a target pH in about 1 hour about 2 hours, about 3 hours, about 4 hours, about 8 hours, about 12 hours, about 16 hours, about 20 hours, or about 24 hours. Suitably, the wound may be an ulcer.

In an embodiment, there may be provided a scaffold comprising an electrospun polymer fiber for use in a method of accelerating and/or improving healing of a wound, wherein the method comprises applying to the wound the scaffold, and allowing at least a portion of the scaffold to degrade, thereby producing a byproduct. The pH of the byproduct may be different from the initial pH of the wound, and producing the byproduct may change the initial pH of the wound. In an embodiment, the byproduct is an alpha-hydroxy acid such as lactic acid, or any other acid produced during degradation of an electrospun scaffold, as described herein. In an embodiment, the wound may be a chronic wound. Suitably, the electrospun polymer fiber may comprise, for example, polyglycolic acid, poly(lactide-co-caprolactone), polylactic acid, polycaprolactone, copolymers thereof, or combinations thereof. Suitably, an electrospun polymer fiber may comprise polyglycolic acid and/or poly(lactide-co-caprolactone). Suitably, a first polymer fiber may comprise polyglycolic acid and a second polymer fiber may comprise poly(lactide-co-caprolactone). Suitably, the acidic by product is an alpha-hydroxy acid such as lactic acid. The diameter of the fibers may be in the range from about 1 μm to about 100 μm. In certain embodiments, the diameter of the fibers may be in the range from about 1 μm to about 5 μm. Suitably, a first electrospun fiber may degrade within 1 hour to 3 days, and a second electrospun fiber may degrade from 3 days to 7 days or longer. Suitably, the scaffold may be configured to provide a reduction in pH to a target pH in about 1 hour about 2 hours, about 3 hours, about 4 hours, about 8 hours, about 12 hours, about 16 hours, about 20 hours, or about 24 hours. Suitably, the wound may be an ulcer.

EXAMPLES

Example 1: Effect of Scaffolds on Local Environments

To assess the effect of a scaffold as described herein on its local environment, five 20 mm×150 mm test tubes were each filled with: 11.25 g deionized water; 1.25 g 10× concentration phosphate buffered saline (PBS); and 0.013 g sodium azide. Teach test tube was gently agitated to mix the contents. The test tubes were then placed into a test tube rack in an incubation chamber set at 37° C., and were allowed to come up to temperature. The temperature of each test tube was confirmed as 37±1° C. using a calibrated temperature probe.

A scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun, was placed in each test tube. Each scaffold measured 7.5 cm×5 cm, a size that was selected to achieve a dosing of 6 cm² surface area (counting both sides of the scaffold) per 1 mL of solution. The fibers of each scaffold had a diameter from about 1 μm to about 3 μm.

The pH of each solution was measured immediately after the placement of the scaffold (t=0 hours), and again at t=6 hours, t=24 hours, t=30 hours, t=49 hours, t=54 hours, t=72 hours, and t=78 hours after the placement of the scaffold. The pH meter was calibrated before each measurement. The resulting pH measurements are shown in Table 1:

TABLE 1

| Time Point (Hours) | Tube 1 pH | Tube 2 pH | Tube 3 pH | Tube 4 pH | Tube 5 pH | Average pH | St. Dev. |
|---|---|---|---|---|---|---|---|
| 0  | 7.63 | 7.63 | 7.62 | 7.63 | 7.62 | 7.63 | 0.01 |
| 6  | 7.09 | 7.08 | 7.11 | 7.09 | 7.09 | 7.09 | 0.01 |
| 24 | 7.05 | 7.01 | 6.98 | 7.02 | 6.96 | 7.00 | 0.04 |
| 30 | 6.94 | 6.91 | 6.83 | 6.92 | 6.83 | 6.89 | 0.05 |
| 49 | 6.50 | 6.57 | 6.26 | 6.55 | 6.32 | 6.44 | 0.14 |
| 54 | 6.38 | 6.46 | 6.16 | 6.44 | 6.19 | 6.33 | 0.14 |
| 72 | 6.08 | 6.17 | 5.87 | 6.08 | 5.87 | 6.01 | 0.14 |
| 78 | 5.98 | 6.06 | 5.76 | 5.95 | 5.78 | 5.91 | 0.13 |

The average pH of the solutions dropped from 7.63±0.01 at t=0 hours to 5.91±0.13 at t=78 hours after the placement of the scaffolds. Therefore, the scaffolds caused a decrease in the pH of each PBS solution.

Example 2: Controlled Degradation of Scaffold

Figure 2:
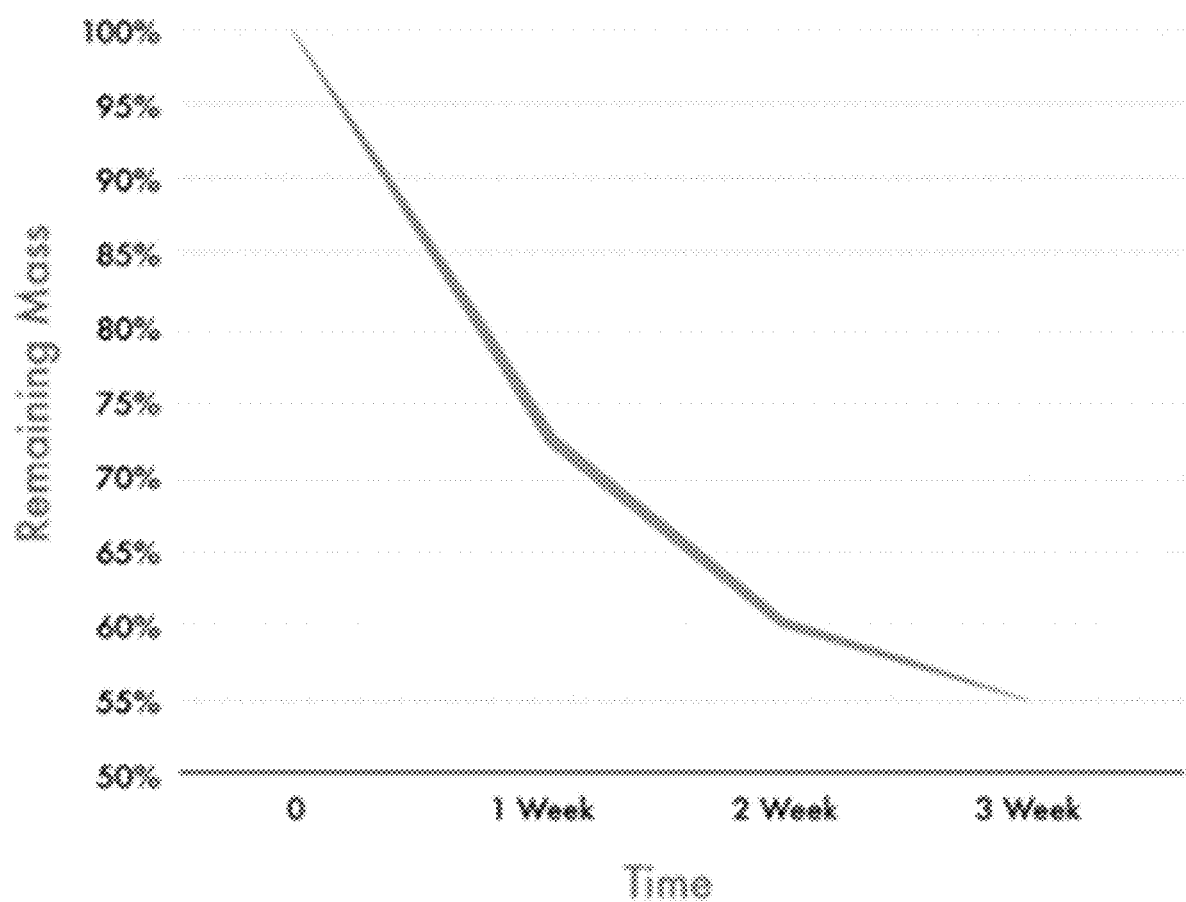
FIG. 2 is a graph showing the degradation of mass of an embodiment of a scaffold as described herein in PBS solution over two weeks.

In vitro degradation tests similar to those described in Example 1 above demonstrate a drop in pH of the local environment from 7.4 to 4.75 over the course of two weeks, and a 40% mass loss of the scaffold over two weeks. FIG. 1 is a graph showing the effect of the degradation of a scaffold as described herein on the pH of a PBS solution over two weeks. Similarly, FIG. 2 is a graph showing the degradation of mass of a scaffold as described herein in PBS solution over two weeks.

Example 3: Case Study: Pressure Ulcer

A 90-year-old Caucasian male subject with paraplegia presented with a right heel pressure ulcer of more than 4 months' duration. Additionally, a 2.2 cm tunnel was observed superomedially upon presentation. Despite receiving the best practice standard of care in addition to advanced modalities, the subject developed osteomyelitis and required surgical debridement. A first scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun, was applied to the wound on Day 0 (7 days after surgical debridement). Robust granulation tissue was noted within days.

A second scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun, was applied to the wound on Day 7, and accelerated progress continued. On Day 42, a 70% decrease in planimetric area was observed. Full wound closure was achieved on Day 77, and was maintained at Day 91 and at Day 121.

Figure 3D:
FIG. 3D shows the pressure ulcer of FIG. 3A on Day 77, with full wound closure.
Figure 3C:
FIG. 3C shows the pressure ulcer of FIG. 3A on Day 42.
Figure 3E:
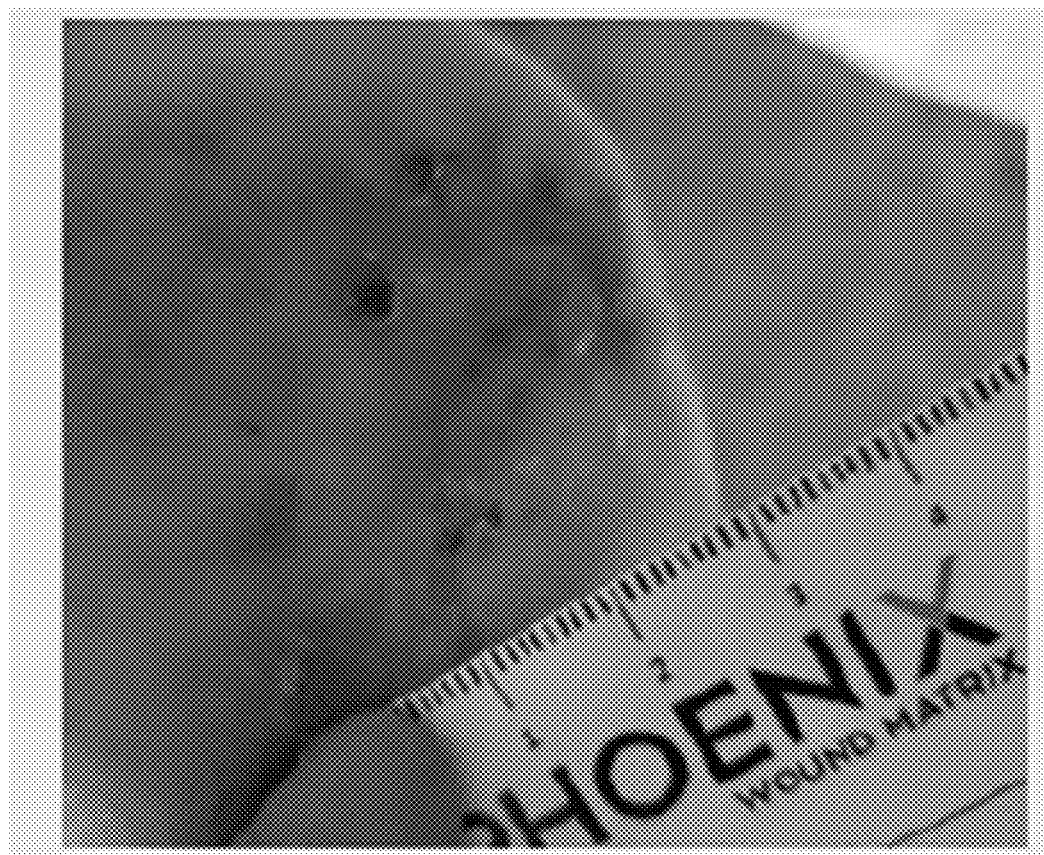
FIG. 3E shows the pressure ulcer of FIG. 3A on Day 91, with maintenance of the full wound closure.

FIG. 3A shows the pressure ulcer on Day 0, having a planimetric area of 11.8 cm². FIG. 3B shows the same pressure ulcer on Day 7, having a planimetric area of 11.3 cm² (i.e., a 4% decrease). FIG. 3C shows the pressure ulcer on Day 42, with a planimetric area of 3.6 cm² (i.e., a 70% decrease). FIG. 3D shows the pressure ulcer on Day 77, with full wound closure. FIG. 3E shows the area on Day 91, with maintenance of the full wound closure. In summary, the wound closure was attained within eleven weeks using two scaffolds as described herein, combined with wound care best practices. This wound closure was attained after the failure of other advanced modalities.

Example 4: Case Study: Necrotizing Fasciitis

A 57-year-old male subject with hypertension and type II diabetes mellitus was diagnosed with necrotizing fasciitis three weeks post-fall on his sacrum. The subject required extensive surgical debridement and treatment with antibiotics. The resulting wound extended from the upper right inguinal region, through the perineum, to the perianal area. Additionally, the subject complained of significant pain. A first scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun, was applied to the anterior aspect of the wound on Day 0. By Day 7, the subject reported a considerable decrease in pain, and healthy granulation tissue was observed developing in the wound bed.

A second scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun, was applied to the wound on Day 11. On Day 32, a 77% decrease in the planimetric area of the anterior wound was observed. A third scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun, was applied to the wound on Day 32. By Day 67, further significant reduction in the planimetric area of the anterior wound was achieved.

Figure 4A:
FIG. 4A shows a wound resulting from necrotizing fasciitis on Day 0 An embodiment of a scaffold as described herein was applied to the pressure ulcer on Day 0.
Figure 4C:
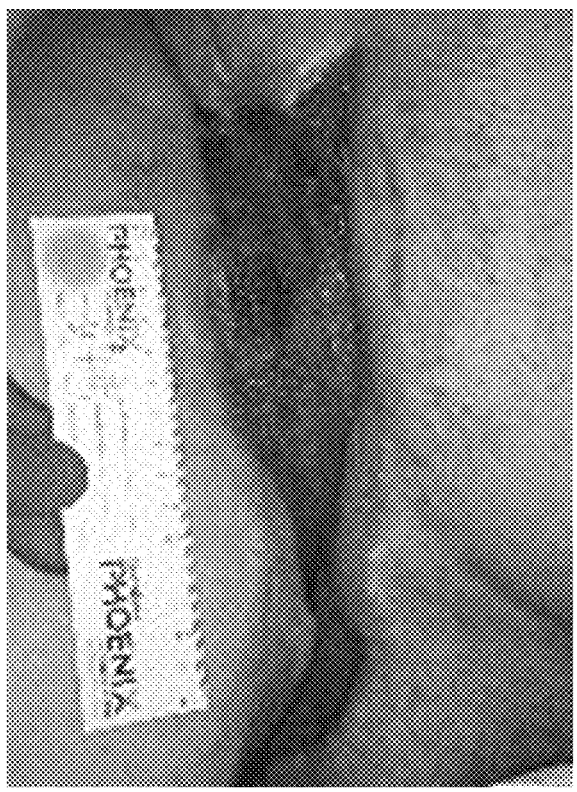
FIG. 4C shows the wound of FIG.
Figure 4B:
FIG. 4B shows the wound of FIG. 4A on Day 11. Another embodiment of a scaffold as described herein was applied to the pressure ulcer on Day 11.
Figure 4E:
FIG. 4E shows the wound on Day 67, with a 96% decrease in the planimetric area of the wound from Day 0.
Figure 4D:
FIG. 4D shows the wound of FIG. 4A on Day 60.

FIG. 4A shows the anterior portion of the wound on Day 0, with a planimetric area of 256.9 cm$^2$. FIG. 4B shows the wound on Day 11, with a planimetric area of 115.7 cm$^2$ (i.e., a 55% decrease). FIG. 4C shows the wound on Day 32, with a planimetric area of 58.4 cm$^2$ (i.e., a 77% decrease). FIG. 4D shows the wound on Day 60, with a planimetric area of 29.8 cm$^2$ (i.e., a 88% decrease). FIG. 4E shows the wound on Day 67, with a planimetric area of 11.4 cm$^2$ (i.e., a 96% decrease). In summary, the subject made remarkable progress within ten weeks with using three scaffolds as described herein, combined with wound care best practices.

Example 5: Second-Degree Burn

A 50-year-old female presented with an acute second-degree burn of 6 days duration to the anterior forearm. A scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun, was applied to the wound 6 days post-trauma (on Day 0). A non-adherent sterile gauze pad was placed over the scaffold, and both were secured with a bandage wrap. The patient reported immediate alleviation of pain following the application of the scaffold. On Day 7, the wound was observed to be healing well. The wound healed within 18 days.

Figure 5B:
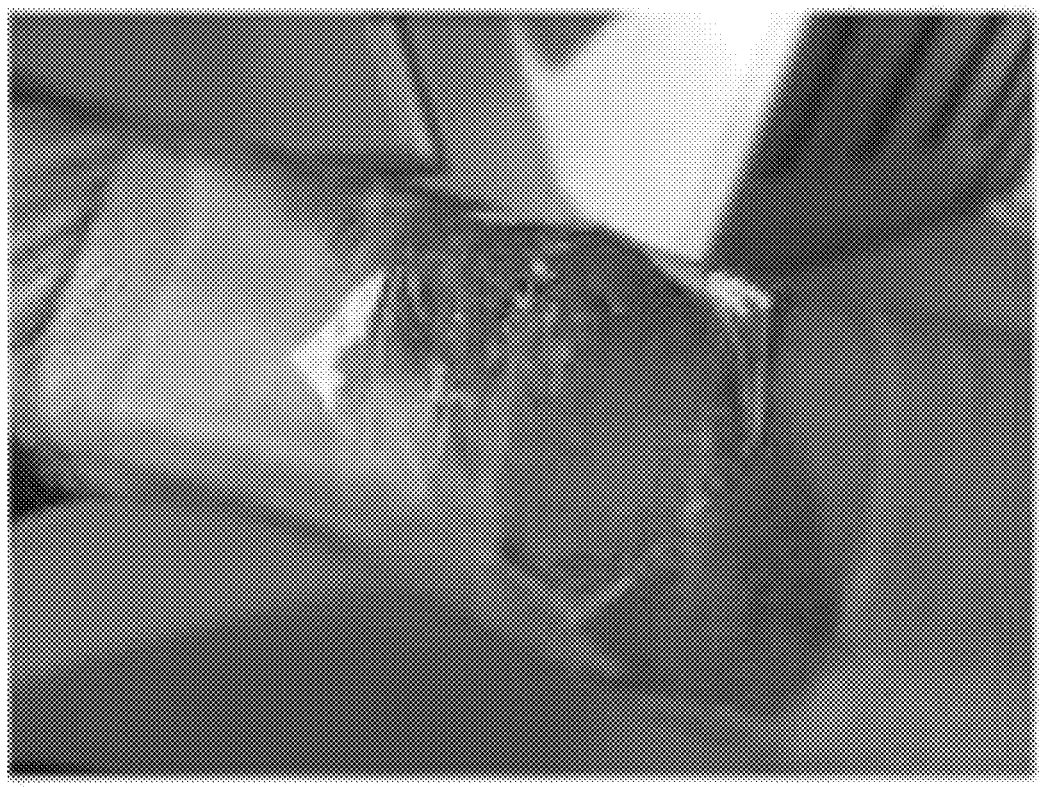
FIG. 5B shows the wound of FIG. 5A on Day 0, when an embodiment of a scaffold as described herein was applied.
Figure 5A:
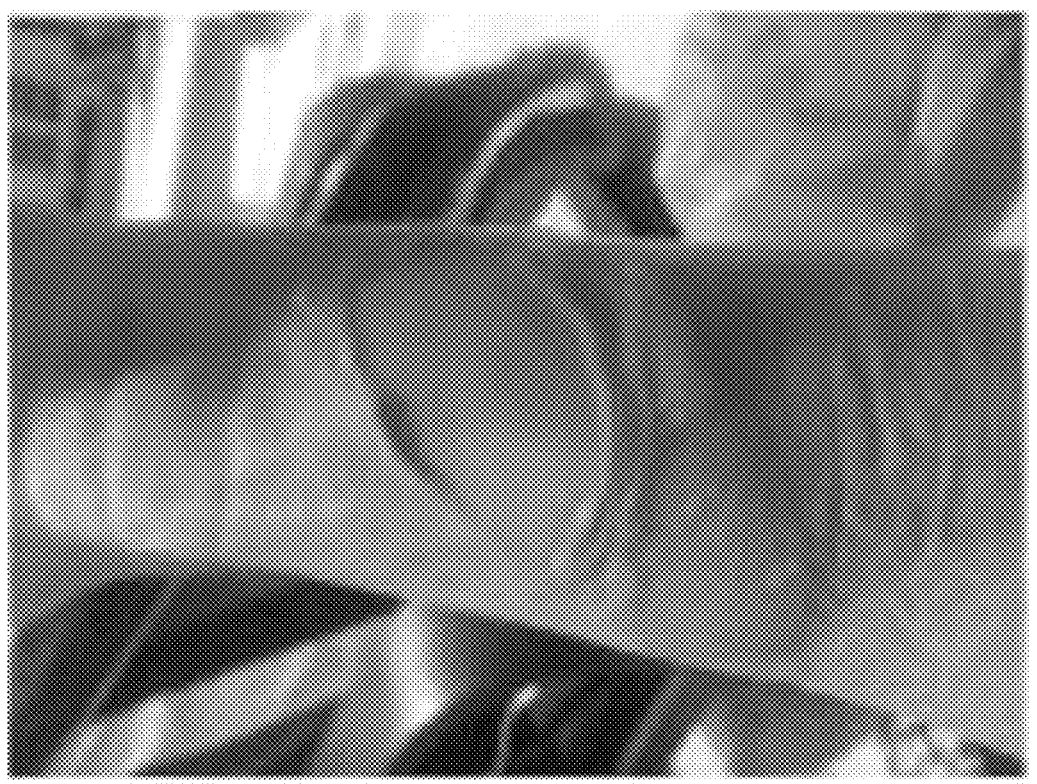
FIG. 5A shows a burn on the day of injury.
Figure 5D:
FIG. 5D shows the wound of FIG. 5A on Day 18 with the wound healed.
Figure 5C:
FIG. 5C shows the wound of FIG. 5A on Day 7.
Figure 5E:
FIG. 5E shows the wound of FIG. 5A after 19.5 weeks, in the tissue remodeling phase.

FIG. 5A shows the wound on the day of injury. FIG. 5B shows the wound on Day 0, with the application of the scaffold. FIG. 5C shows the wound on Day 7, and FIG. 5D shows the wound on Day 18 with the wound healed. FIG. 5E shows the wound after 19.5 weeks, in the tissue remodeling phase.

Example 6: Pressure Ulcer Complicated by Charcot-Marie-Tooth Disease

A sixty-six year old male with Charcot-Marie-Tooth (CMT) disease, peripheral neuropathy, and neurological issues presented on Day 0 with a plantar pressure ulcer over the left fifth metatarsal. The wound measured 3.3 cm×3.3 cm×0.2 cm. Sharp debridement was performed, followed by application of becaplermin gel (recombinant PDGF) and a scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun. The patient was not a candidate for total contact casting; bolstered padding was utilized to offload. By Day 10, a 28% reduction in total wound size was noted with wound measuring 2.8 cm×2.8 cm×0.2 cm. By Day 35, complete wound closure was achieved. On further evaluation at Day 50, the wound remained closed and continued healthy tissue remodeling was noted.

Figure 6A:
FIG. 6A shows an ulcer at Day 0, when an embodiment of a scaffold as described herein was applied.
Figure 6C:
FIG. 6C shows the wound of FIG. 6A closed at Day 35.
Figure 6B:
FIG. 6B shows the wound of FIG. 6A at Day 10.
Figure 6D:
FIG. 6D shows the wound of FIG. 6A remained closed at Day 50.

FIG. 6A shows the ulcer at Day 0, with a planimetric area of 10.89 cm$^2$. A first scaffold was applied at Day 0. FIG. 6B shows the wound at Day 10, with a planimetric area of 7.84 cm$^2$ (i.e., a 28% decrease). FIG. 6C shows the wound closed at Day 35, and FIG. 6D shows the wound remained closed at Day 50.

In summary, the patient received a scaffold as described herein as the first-line treatment option, and the wound closure was achieved in five weeks with applications of a first, second, and third scaffold.

Example 7: Surgical Wound

A 54-year-old male presented following a transmetatarsal amputation (TMA) of the left foot. The planimetric area of the wound on Day 0 measured 17.2 cm$^2$. The treatment protocol included the standard of care, sharp debridement, moisture management, multi-layer compression, remote ischemic preconditioning (RIPC) and total contact casting. After wound demonstrated only 32% area reduction over 2 months, a first scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun, was applied (Day 0). By Day 7, development of healthy granulation tissue was observed. By Day 18, following the application of a second scaffold and a third scaffold, accelerated healing was observed with a 52% reduction in wound area. Wound closure was achieved with on Day 88 after the application of six total scaffolds.

Figure 7A:
FIG. 7A shows a wound shortly after surgical amputation.
Figure 7C:
FIG. 7C shows the wound of FIG. 7A 59 days after amputation, at which time an embodiment of a scaffold as described herein was applied (scaffold Day 0).
Figure 7B:
FIG. 7B shows the wound of FIG. 7A 45 days after amputation.
Figure 7E:
FIG. 7E shows the wound of FIG. 7A at scaffold Day 25.
Figure 7D:
FIG. 7D shows the wound of FIG. 7A at scaffold Day 18.
Figure 7G:
FIG. 7G shows the wound of FIG. 7A at scaffold Day 88, with wound closure.
Figure 7F:
FIG. 7F shows the wound of FIG. 7A at scaffold Day 46.

FIG. 7A shows the wound shortly after surgical amputation, with a planimetric area of 17.2 cm$^2$. FIG. 7B shows the wound 45 days after amputation, with a planimetric area of 16.68 cm$^2$ (i.e., a 3% decrease). FIG. 7C shows the wound 59 days after amputation, with a planimetric area of 11.7 cm$^2$ (i.e., a 32% decrease). A first scaffold was applied at Day 59, and the day count was restarted at Day 0. A second scaffold and a third scaffold were applied between Day 0 and Day 18. FIG. 7D shows the wound at Day 18, with a planimetric area of 5.57 cm$^2$ (i.e., a 52% decrease). A fourth scaffold was applied at Day 18. FIG. 7E shows the wound at Day 25, with a planimetric area of 4.57 cm² (i.e., a 61% decrease). A fifth scaffold was applied at Day 25. FIG. 7F shows the wound at Day 46, with a planimetric area of 3.32 cm² (i.e., a 72% decrease). FIG. 7G shows the wound at Day 88, with wound closure.

Table 2 below summarizes the patient's healing before and after the application of scaffolds as described herein.

| Treatment Period | Day | Reduction in Wound Planimetric Area (%) |
|---|---|---|
| Prior to use of scaffold | 45 | 3% |
| Prior to use of scaffold | 59 | 32% |
| After first scaffold application | 18 | 52% |
| After second scaffold application | 46 | 72% |
| After third scaffold application | 59 | 79% |

Example 8: Trauma Injury

A 10-year-old female sustained a traumatic injury to her left anteromedial leg following a fall from a horse. The patient's injuries involved tissue damage consistent with a crush injury and a significant laceration. Two weeks after the date of injury, the patient required extensive surgical debridement of a failed flap repair and HBOT and NPWT were initiated. One month after the injury (two weeks after surgery), a scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun, was applied. HBOT and NPWT were continued. This patient made steady progress, achieving wound closure on Day 77 with the application of only one scaffold.

Figure 8A:
FIG. 8A shows a traumatic wound on Day 0, at which time an embodiment of a scaffold as described herein was applied.
Figure 8B:
FIG. 8B shows the wound of FIG. 8A at Day 35.
Figure 8D:
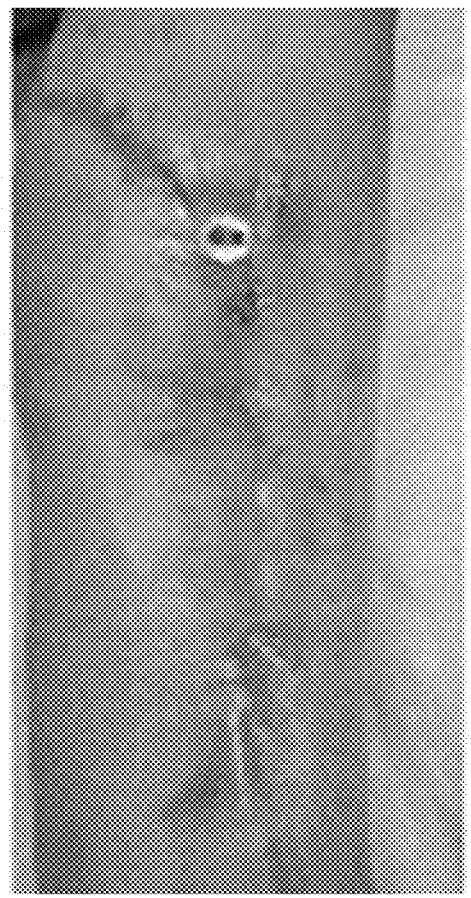
FIG. 8D shows the wound of FIG. 8A at Day 77, with wound closure.
Figure 8C:
FIG. 8C shows the wound of FIG. 8A at Day 62.

FIG. 8A shows the wound on scaffold Day 0, with a planimetric area of 39 cm². A scaffold was applied to the wound at Day 0. FIG. 8B shows the wound at Day 35, with a planimetric area of 14.9 cm² (i.e., a 62% reduction). FIG. 8C shows the wound at Day 62, with a planimetric area of <1 cm² (i.e., a 99% reduction). FIG. 8D shows the wound at Day 77, with wound closure.

Example 9: Bilateral Neuropathic Diabetic Foot Ulcers Complicated by Charcot Joint A 53-year-old male presented with bilateral diabetic foot ulcers (DFU), history of Charcot neuropathic osteoarthropathy (right foot), and a BMI of 33.4. The ulcers failed 8 weeks of antibiotics, silver alginate and offloading with Crowe Walker® (right foot). The right foot wound area decreased 70% following 2 weeks of treatment with a scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun. Wound closure was achieved on Day 36. The left foot wound area decreased 62% following 4 weeks of treatment with a scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun. Wound closure was achieved on Day 71.

Figure 9A:
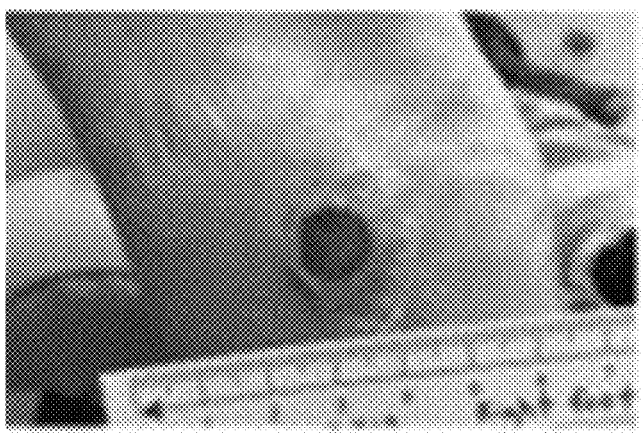
FIG. 9A shows an ulcer on a right foot at Day 0, at which time an embodiment of a scaffold as described herein was applied.
Figure 9B:
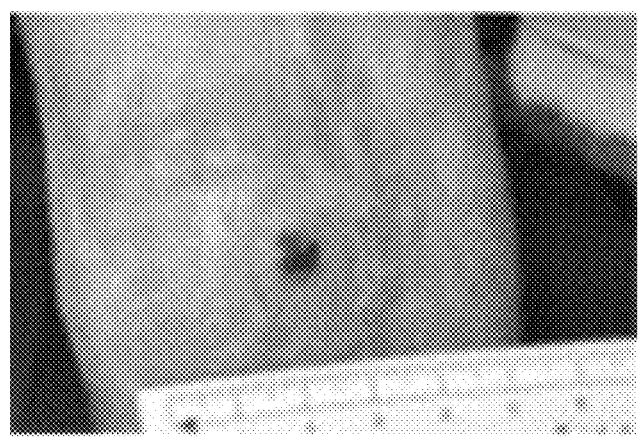
FIG. 9B shows the ulcer of FIG. 9A at Day 13.
Figure 9D:
FIG. 9D shows the ulcer of FIG. 9A at Day 36, with wound closure.
Figure 9C:
FIG. 9C shows the ulcer of FIG. 9A at Day 28, with a planimetric area of 0.10 cm$^2$ (i.e., a 91% reduction).

FIG. 9A shows the ulcer on the right foot at Day 0, with a planimetric area of 1.09 cm². FIG. 9B shows the ulcer on the right foot at Day 13, with a planimetric area of 0.33 cm² (i.e., a 70% reduction). FIG. 9C shows the ulcer on the right foot at Day 28, with a planimetric area of 0.10 cm² (i.e., a 91% reduction). FIG. 9D shows the ulcer on the right foot at Day 36, with wound closure.

Figure 9F:
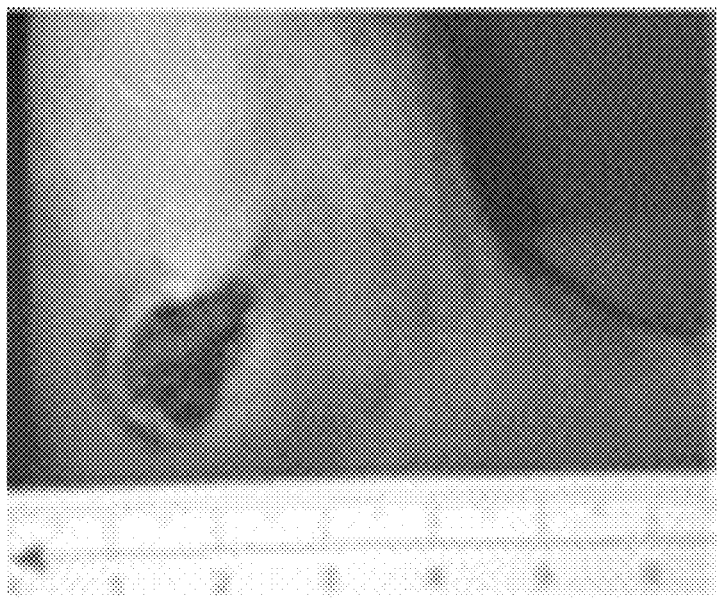
FIG. 9F shows the ulcer of FIG. 9E on Day 28.
Figure 9E:
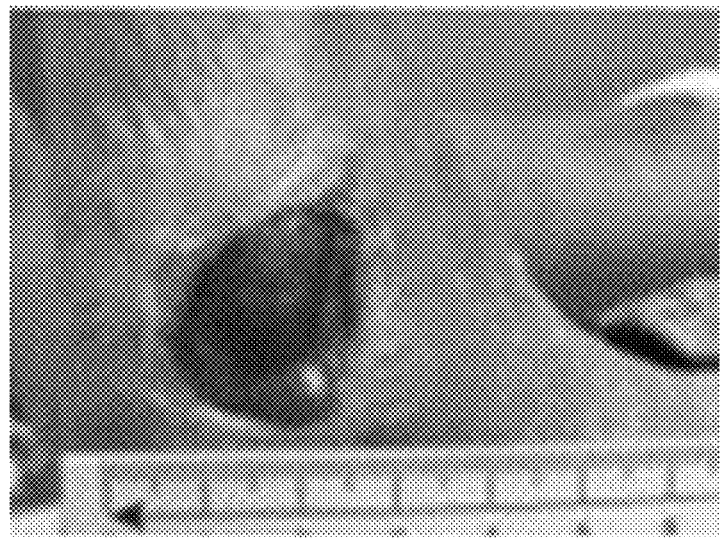
FIG. 9E shows an ulcer on a left foot at Day 0, at which time an embodiment of a scaffold as described herein was applied.
Figures 9G, 9H:
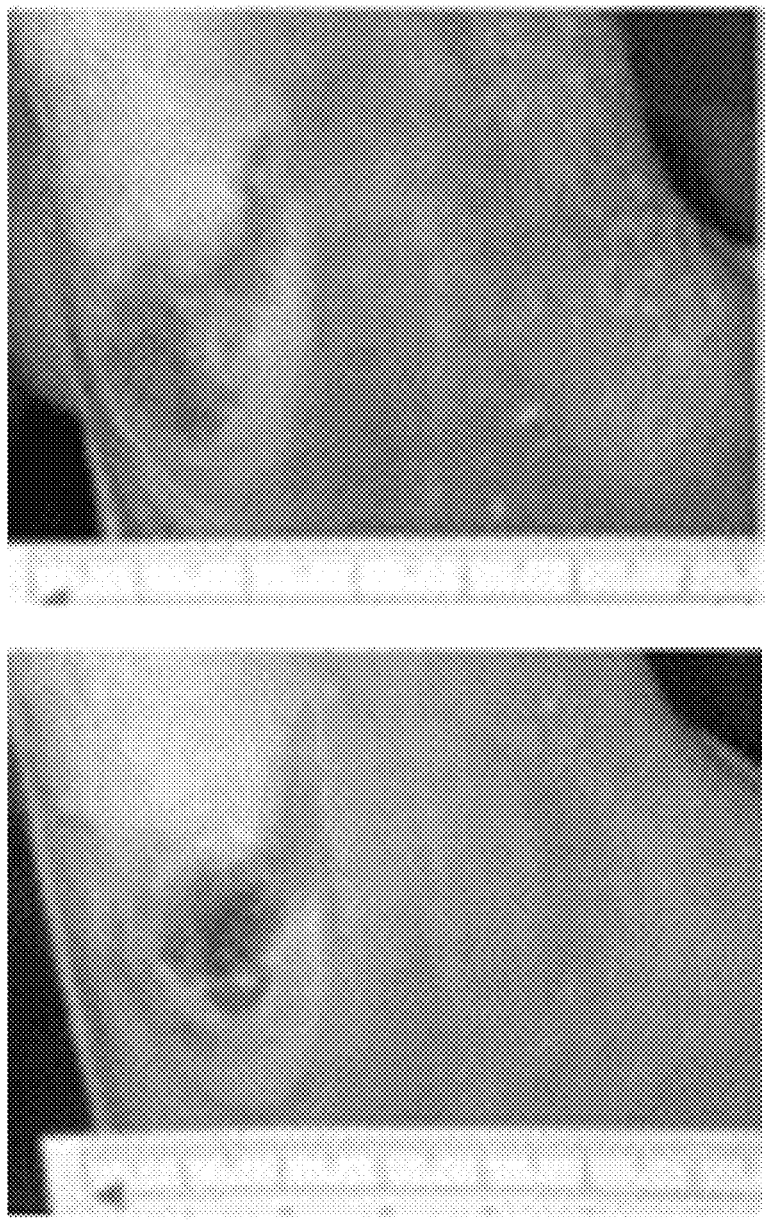
FIG. 9G shows the ulcer of FIG. 9E at Day 43.
FIG. 9H shows the ulcer of FIG. 9E at Day 71, with wound closure.

FIG. 9E shows the ulcer on the left foot on Day 0, with a planimetric area of 3.78 cm². FIG. 9F shows the ulcer on the left foot on Day 28, with a planimetric area of 1.48 cm² (i.e., a 62% reduction). FIG. 9G shows the ulcer on the left foot at Day 43, with a planimetric area of 1.03 cm² (i.e., a 73% reduction). FIG. 9H shows the ulcer of the left foot at Day 71, with wound closure.

Example 10: Vascular Ulcer of Mixed Etiology

A 66-year-old male with history of recurrent leg ulcers and multiple comorbidities including type 2 diabetes, congestive heart failure, peripheral artery disease, peripheral neuropathy, and hypertension, presented with a right, lower leg venous ulcer measuring 3.3×6.2×0.2 cm. A scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun, was applied as first-line therapy on Day 0, along with becaplermin gel (recombinant PDGF). By Day 7, a 33% reduction in wound size was noted, measuring 2.5×5.5×0.1 cm. Wound closure was achieved in 28 days with the application of two additional scaffolds. One week post-closure, the patient presented with a recurrence measuring 1.1×1.1×0.1 cm. A fourth scaffold was applied, and wound closure was achieved in 3 weeks.

Figure 10A:
FIG. 10A shows an ulcer at Day 0, at which time an embodiment of a scaffold as described herein was applied.
Figure 10B:
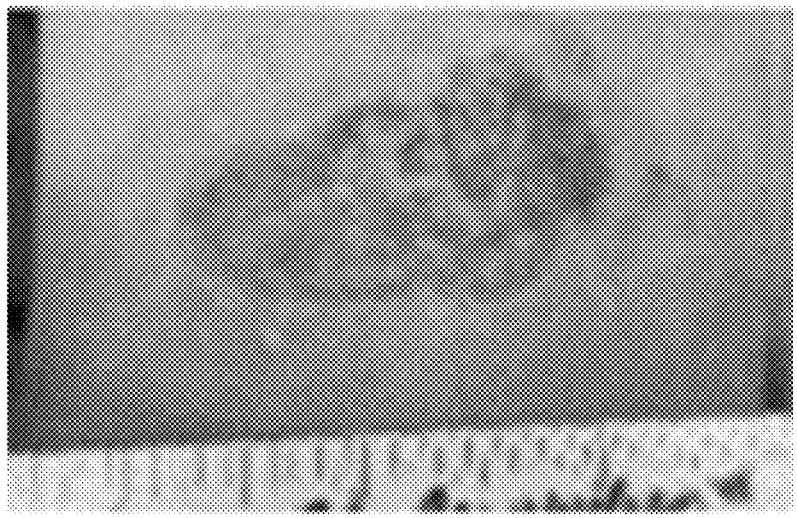
FIG. 10B shows the ulcer of FIG. 10A at Day 7, at which time a second embodiment of a scaffold as described herein was applied.
Figure 10D:
FIG. 10D shows the ulcer of FIG. 10A at Day 28, with wound closure.
Figure 10C:
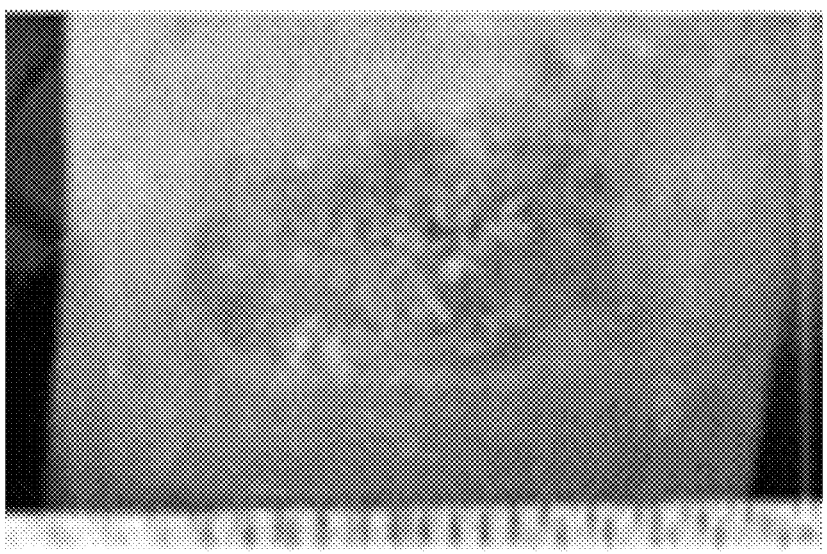
FIG. 10C shows the ulcer of FIG. 10A at Day 22, at which time a third embodiment of a scaffold as described herein was applied.
Figure 10E:
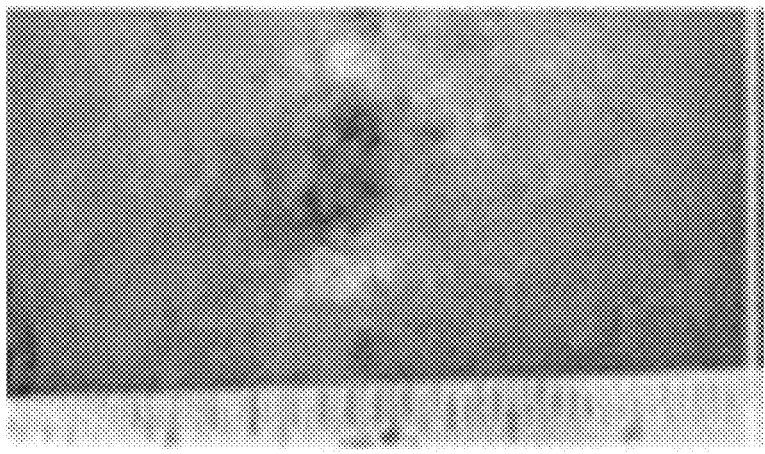
FIG. 10E shows the recurrence of the ulcer of FIG. 10A at Day 0, at which time another embodiment of a scaffold as described herein was applied.
Figure 10F:
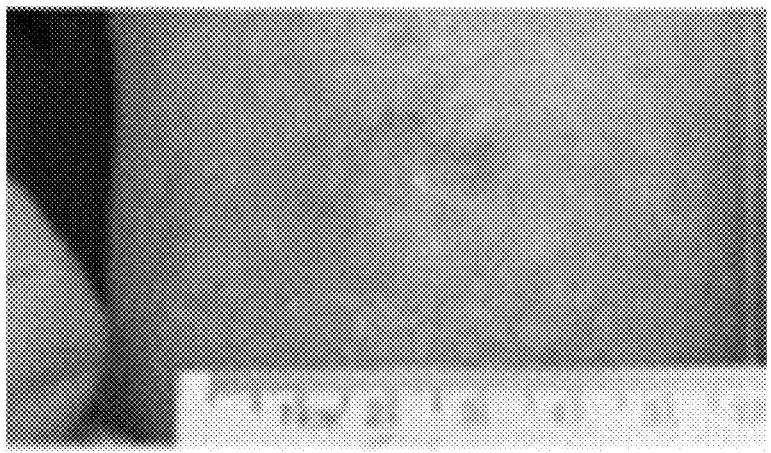
FIG. 10F shows the recurred ulcer of FIG. 10E at day 21, with wound closure.

FIG. 10A shows the ulcer at Day 0, with a planimetric area of 20.46 cm². A first scaffold was applied at Day 0. FIG. 10B shows the ulcer at Day 7, with a planimetric area of 13.75 cm² (i.e., a 33% reduction). A second scaffold was applied at Day 7. FIG. 10C shows the ulcer at Day 22, with a planimetric area of 12.6 cm² (i.e., a 38% reduction). A third scaffold was applied at Day 22. FIG. 10D shows the ulcer at Day 28, with wound closure. FIG. 10E shows the recurrence of the ulcer at Day 0, with a planimetric area of 1.21 cm². FIG. 10F shows the recurred ulcer at day 21, with wound closure.

Example 11: Neuropathic Diabetic Foot Ulcer

A 51-year-old male presented with a chronic diabetic foot ulcer (DFU), of over 2 months duration, due to a traumatic puncture wound to the lateral left foot plantar surface. The patient had a history of peripheral neuropathy, hypertension, a BMI of 40, osteomyelitis, and underwent resection of 5$^{th}$ metatarsal head followed by 6 weeks of IV antibiotic therapy. A scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun, was applied 8 weeks post-surgery. The wound healed in 6 weeks with the application of three total scaffolds.

Figures 11A, 11B:
FIG. 11A shows an ulcer at Day 0, at which time an embodiment of a scaffold as described herein was applied.
FIG. 11B shows the ulcer of FIG. 11A at Day 7, at which time a second embodiment of a scaffold as described herein was applied.
Figure 11C:
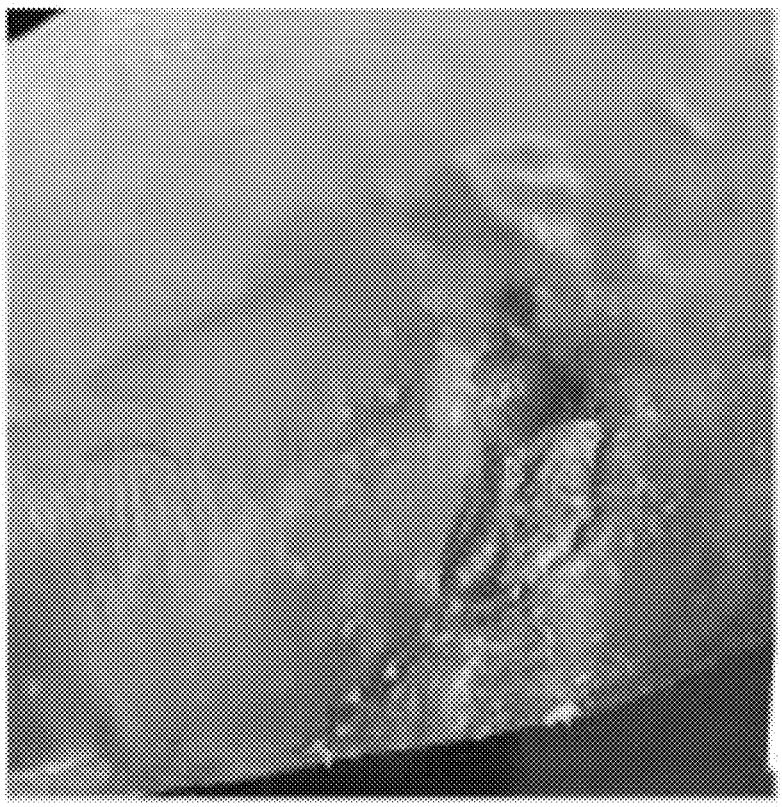
FIG. 11C shows the ulcer of FIG. 11A at Day 14, at which time third second embodiment of a scaffold as described herein was applied.
Figure 11D:
FIG. 11D shows the ulcer of FIG. 11A at Day 42, with wound closure.

FIG. 11A shows the ulcer at Day 0, with a planimetric area of 2.44 cm². The first scaffold was applied at Day 0. FIG. 11B shows the ulcer at Day 7, with a planimetric area of 1.75 cm² (i.e., a 28% reduction). A second scaffold was applied at Day 7. FIG. 11C shows the ulcer at Day 14, with a planimetric area of 1.38 cm² (i.e., a 43% reduction). A third scaffold was applied at Day 14. FIG. 11D shows the ulcer at Day 42, with wound closure.

Example 12: Diabetic Food Ulcer with Trauma

A 40-year-old female with a history of type 1 diabetes, multiple sclerosis, and Raynaud's disease, presented to the wound care clinic after a fall 4 weeks earlier. Following thorough debridement, a scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun, was applied. Wound depth was visibly reduced within 1 week of treatment. The planimetric area decreased by 43% after 2 weeks of treatment and the application of two total scaffolds. The wound closed following 49 days of treatment.

Figure 12B:
FIG. 12B shows the ulcer of FIG. 12A at Day 7, at which time a second embodiment of a scaffold as described herein was applied.
Figure 12A:
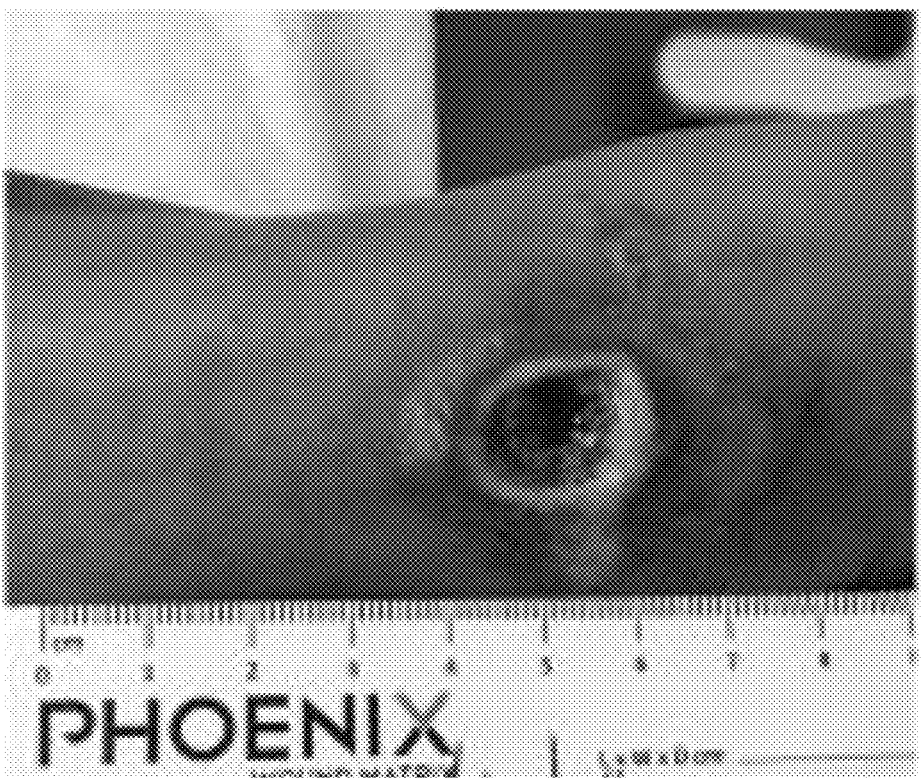
FIG. 12A shows an ulcer at Day 0, at which time an embodiment of a scaffold as described herein was applied.
Figure 12D:
FIG. 12D shows the ulcer of FIG. 12A at Day 49, with wound closure.
Figure 12C:
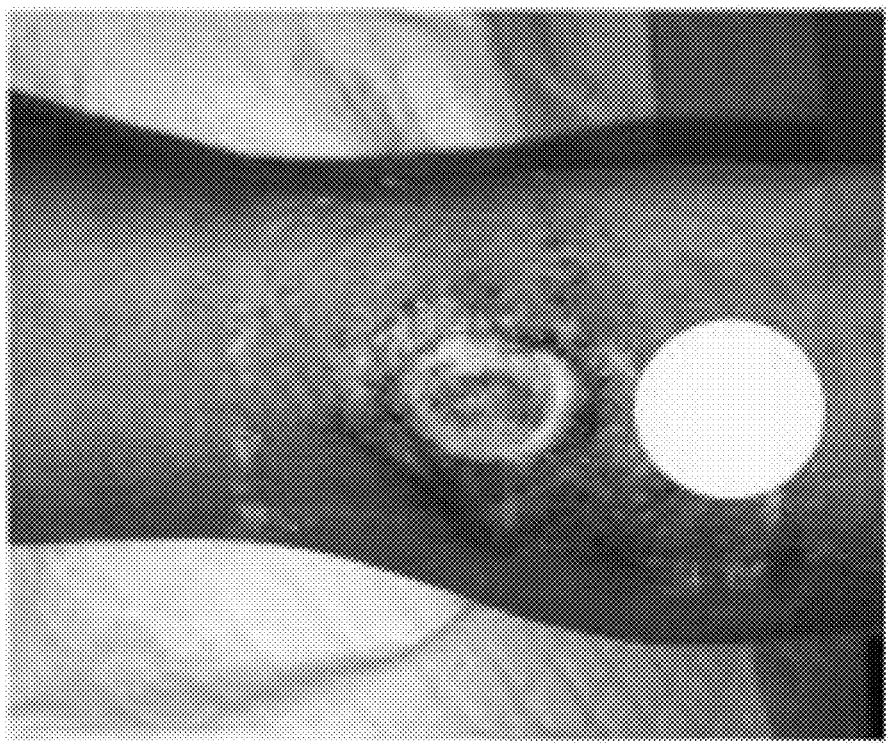
FIG. 12C shows the ulcer of FIG. 12A at Day 14.

FIG. 12A shows the ulcer at Day 0, with a planimetric area of 1.63 cm². The first scaffold was applied at Day 0. FIG. 12B shows the ulcer at Day 7, with a planimetric area of 1.51 cm² (i.e., a 7% reduction). A second scaffold was applied at Day 7. FIG. 12C shows the ulcer at Day 14, with a planimetric area of 0.86 cm² (i.e., a 43% reduction). FIG. 12D shows the ulcer at Day 49, with wound closure.

Example 13: Ischemic, Neuropathic Diabetic Foot Ulcer

A 74-year-old male with type 2 diabetes, severe peripheral artery disease resulting in markedly inadequate perfusion status, and peripheral neuropathy presented with 5 ischemic diabetic toe ulcers of the left foot, after having failed the standard of care for 4 weeks. Prior consult recommended amputation of the gangrenous $2^{nd}$ and $4^{th}$ toes. Collectively, wound areas measured 26.18 cm². On Day 0, sharp debridement was performed and a scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun, was applied. By Day 7, epithelialization of Hallux and 5th toe wounds was achieved, along with a 44% reduction in combined wound area. By Day 36, the Hallux and 5th toe remained epithelialized and a combined wound area reduction of 64% noted. Patient continued to respond well to treatment with the scaffold, achieving an 85% reduction in combined wound area in 12 weeks. 100% reduction in combined wound area was achieved in 22 weeks with closure of the 2 initially gangrenous toes.

Figure 13B:
FIG. 13B shows the wound area of FIG. 13A at Day 7, at which time a second embodiment of a scaffold as described herein was applied.
Figure 13A:
FIG. 13A shows a wound area at Day 0, at which time an embodiment of a scaffold as described herein was applied.
Figure 13D:
FIG. 13D shows the wound area of FIG. 13A at Day 49, at which time an eighth embodiment of a scaffold as described herein was applied.
Figure 13C:
FIG. 13C shows the wound area of FIG. 13A at Day 36, at which time a sixth embodiment of a scaffold as described herein was applied.
Figure 13F:
FIG. 13F shows the wound area of FIG. 13A with wound closure.
Figure 13E:
FIG. 13E shows the wound area of FIG. 13A at Day 84.

FIG. 13A shows the wound area at Day 0. A first scaffold was applied at Day 0. FIG. 13B shows the wound area at Day 7, with a reduction in planimetric area of 44%. A second scaffold was applied at Day 7. A third, fourth, and fifth scaffold were applied between Day 7 and Day 36. FIG. 13C shows the wound area at Day 36, with a reduction in planimetric area of 64%. A sixth scaffold was applied at Day 36. A seventh scaffold was applied between Day 36 and Day 49. FIG. 13D shows the wound area at Day 49, with a reduction in planimetric area of 69%. An eighth scaffold was applied at Day 49. FIG. 13E shows the wound area at Day 84, with a reduction in planimetric area of 85%. FIG. 13F shows the wound area with wound closure (epithelialization across the wound).

Example 14: Arterial Leg Ulcer

An 84-year-old male with peripheral artery disease, coronary artery disease, and peripheral neuropathy presented with a left lower leg ischemic ulcer measuring 3.7×3.6×0.1 cm. A scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun, was applied on Day 0. On Day 4, a 24% reduction in wound area was noted. The matrix was still visible on the wound bed, therefore, no new scaffold was applied. On Day 11, accelerated wound healing was noted with an 97% reduction in wound area. Wound closure was achieved on Day 25.

Figure 14A:
FIG. 14A shows an ulcer on Day 0, at which time an embodiment of a scaffold as described herein was applied.
Figure 14B:
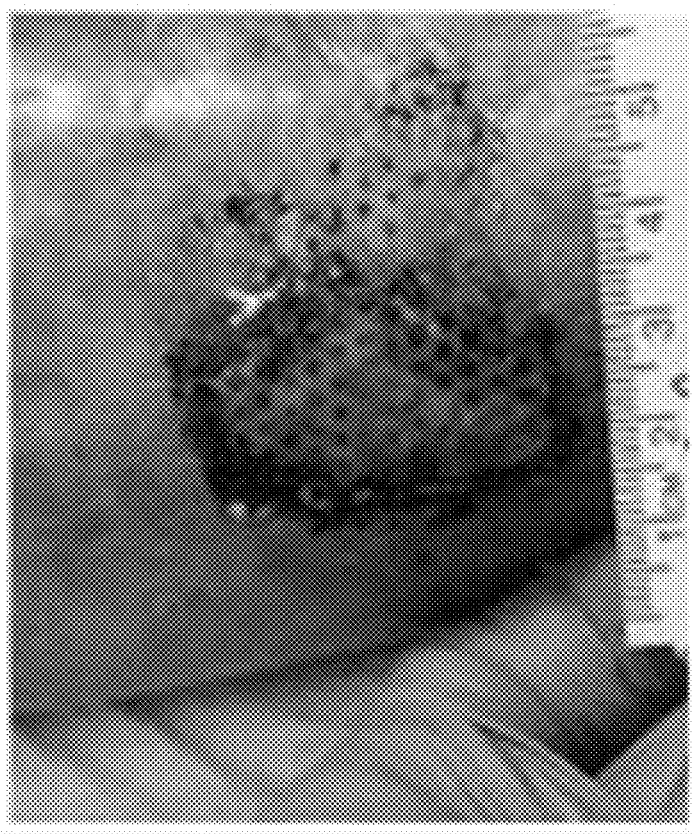
FIG. 14B shows the ulcer of FIG. 14A on Day 7.
Figure 14D:
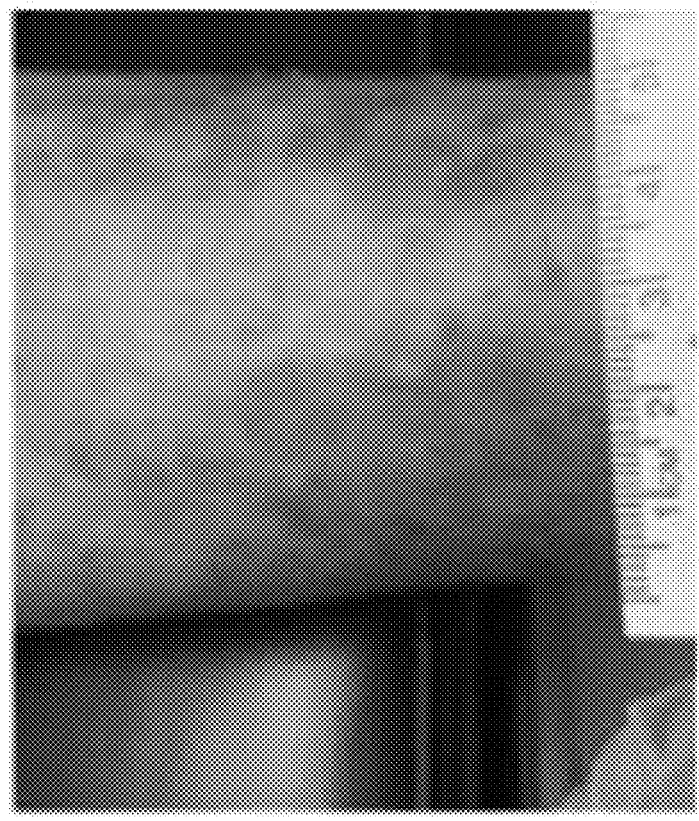
FIG. 14D shows the ulcer of FIG. 14A at Day 25, with wound closure.
Figure 14C:
FIG. 14C shows the ulcer of FIG. 14A on Day 11 at which time a second embodiment of a scaffold as described herein was applied.

FIG. 14A shows the ulcer on Day 0, with a planimetric area of 14.06 cm². A scaffold was applied at Day 0. FIG. 14B shows the ulcer on Day 7, with a planimetric area of 10.64 cm² (i.e., a 24% reduction). FIG. 14C shows the ulcer on Day 11, with a planimetric area of 0.35 cm² (i.e., a 97% reduction). A second scaffold was applied at Day 11. FIG. 14D shows the ulcer at Day 25, with wound closure.

Example 15: Post-Surgical Diabetic Foot Ulcer

A 68-year-old female with a history of type 2 diabetes, hypertension, obesity, osteomyelitis and resection of 5th metatarsal head, followed by 6 weeks IV of antibiotic therapy, required treatment of a post-surgical diabetic foot ulcer of the left medial arch. A scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun, was applied on Day 0, which was eight weeks after metatarsal resection surgery. 70% wound area reduction was achieved in 20 days, with wound closure occurring on Day 41 of scaffold application.

Figure 15D:
FIG. 15D shows the ulcer of FIG. 15A at Day 27, at which time a fifth embodiment of a scaffold as described herein was applied.
Figure 15C:
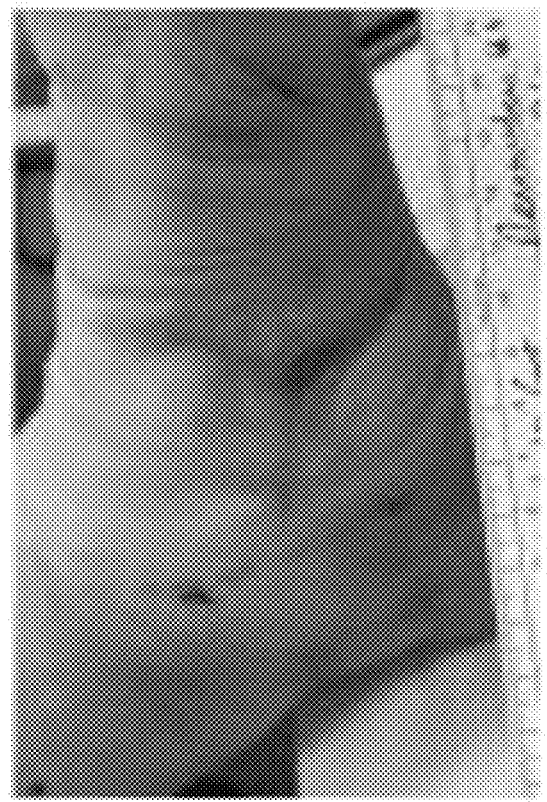
FIG. 15C shows the ulcer of FIG. 15A at Day 20, at which time a fourth embodiment of a scaffold as described herein was applied.
Figure 15E:
FIG. 15E shows the ulcer of FIG. 15A at Day 41, with wound closure.

FIG. 15A shows the ulcer on Day 0, with a planimetric area of 1.08 cm². A scaffold was applied at Day 0. A second scaffold was applied between Day 0 and Day 13. FIG. 15B shows the ulcer at Day 13, with a planimetric area of 0.9 cm² (i.e., a 17% reduction). A third scaffold was applied at Day 13. FIG. 15C shows the ulcer at Day 20, with a planimetric area of 0.32 cm² (i.e., a 70% reduction). A fourth scaffold was applied at Day 20. FIG. 15D shows the ulcer at Day 27, with a planimetric area of 0.14 cm² (i.e., an 87% reduction). A fifth scaffold was applied at Day 27. FIG. 15E shows the ulcer at Day 41, with wound closure.

Example 16: Sacral Pressure Ulcer

A 90-year-old female, with a history of peripheral artery disease (PAD), coronary artery disease (CAD) and after a hip fracture, presented with a sacral pressure ulcer. Last debridement of wound occurred 1 month earlier at another facility. The patient was admitted to the hospital where healing progress was made until issues with incontinence impacted the wound environment. A scaffold as described herein, comprising an electrospun polymer fiber, wherein the electrospun polymer fiber comprises a first fiber comprising polyglycolic acid and a second fiber comprising poly(lactide-co-caprolactone), and wherein the first fiber and the second fiber are co-spun, was applied on Day 0, and remarkable improvement was observed despite challenges with effective off-loading. Wound closure was attained on Day 76 with a single scaffold application.

Figure 16A:
FIG. 16A shows a pressure ulcer at Day 0, at which time an embodiment of a scaffold as described herein was applied.
Figure 16C:
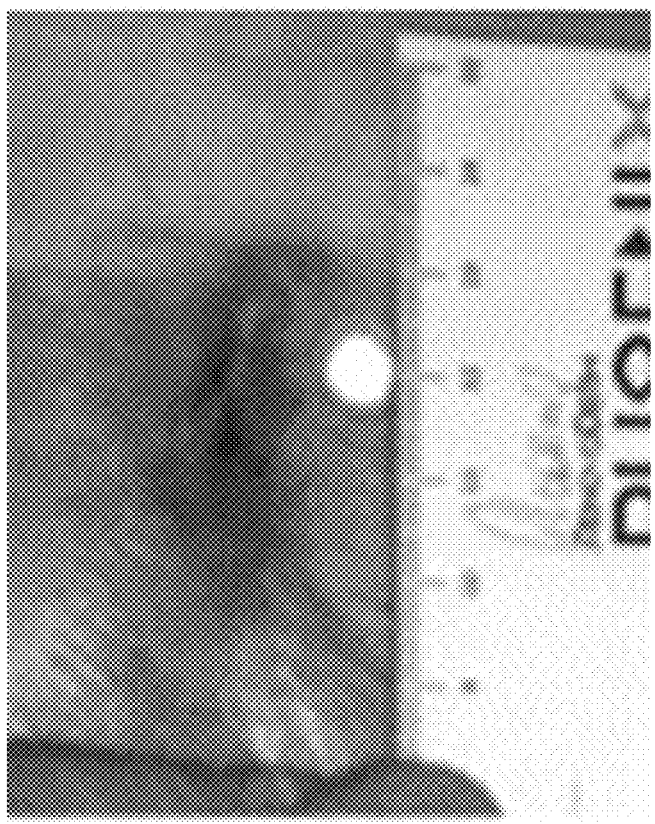
FIG. 16C shows the pressure ulcer of FIG. 16A at Day 34.
Figure 16B:
FIG. 16B shows the pressure ulcer of FIG. 16A at Day 9.
Figure 16E:
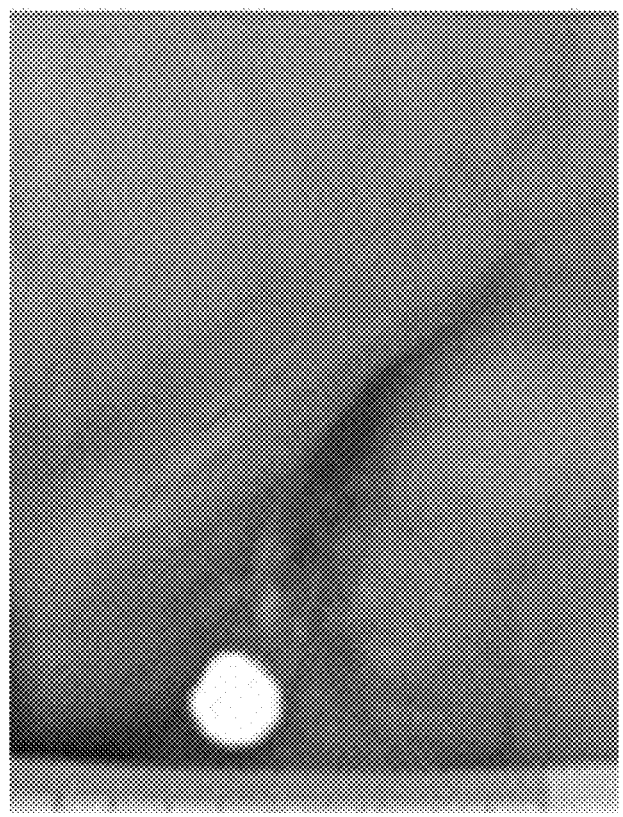
FIG. 16E shows the pressure ulcer of FIG. 16A at Day 76, with wound closure.
Figure 16D:
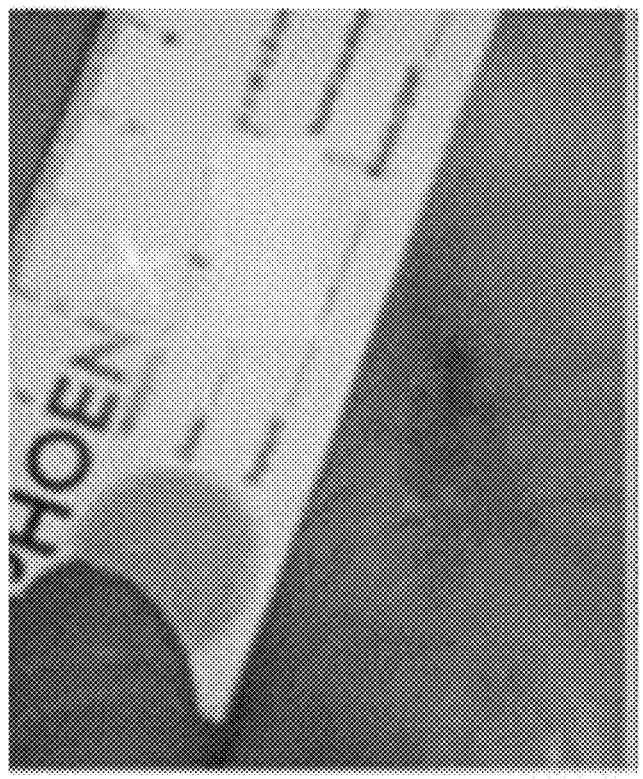
FIG. 16D shows the pressure ulcer of FIG. 16A at Day 55.

FIG. 16A shows the pressure ulcer at Day 0, with a planimetric area of 5.2 cm². A scaffold was applied at Day 0. FIG. 16B shows the pressure ulcer at Day 9, with a planimetric area of 2.6 cm² (i.e., a 49% reduction). FIG. 16C shows the pressure ulcer at Day 34, with a planimetric area of 0.6 cm² (i.e., an 89% reduction). FIG. 16D shows the pressure ulcer at Day 55, with a planimetric area of 0.06 cm² (i.e., a 99% reduction). FIG. 16E shows the pressure ulcer at Day 76, with wound closure.

Finally, Table 3 below includes a summary of the data from the case studies presented in Examples 3-16 herein.

TABLE 3

|  | All Cases | Pressure Ulcers | Diabetic/ Complex Ulcers | Vascular/ Mixed | Surgical Wound | Trauma Wound | Necrotizing Fasciitis Wound | Burn |
|---|---|---|---|---|---|---|---|---|
| Patients | 14 | 3 | 5 | 2 | 1 | 1 | 1 | 1 |
| Wounds | 19 | 3 | 10 | 2 | 1 | 1 | 1 | 1 |
| Wound Granulation | 100% | 100% | 100% | 100% | 100% | 100% | 100% | 100% |
| Area Reduction at 35 Days (%) | 82% | 82% | 81% | 100% | 62% | 62% | 77% | 100% |
| Closure/Area Reduction (%) | 100% | 100% | 100% | 100% | 100% | 100% | 100% | 100% |
| Side Effects | 0 | 0 | 0 | 0 | 0 | 0 | 0 | 0 |
| Adverse Events | 0 | 0 | 0 | 0 | 0 | 0 | 0 | 0 |

All fourteen cases achieved wound closure with no reported side effects or adverse events.

While the present disclosure has been illustrated by the description of exemplary embodiments thereof, and while the embodiments have been described in certain detail, it is not the intention of the Applicant to restrict or in any way limit the scope of the appended claims to such detail. Additional advantages and modifications will readily appear to those skilled in the art. Therefore, the disclosure in its broader aspects is not limited to any of the specific details, representative devices and methods, and/or illustrative examples shown and described. Accordingly, departures may be made from such details without departing from the spirit or scope of the Applicant's general inventive concept.

The invention claimed is:

1. A method of reducing an initial pH of a wound, the method comprising:
    applying a scaffold to the wound, the scaffold comprising fiber fragments, the fiber fragments comprising at least a first electrospun polymer and a second electrospun polymer, wherein the first electrospun polymer and the second electrospun polymer comprise a polymer selected from the group consisting of polyglycolic acid, poly(lactide-co-caprolactone), polydioxanone, and poly(lactide-co-glycolide); and
    allowing at least a portion of the scaffold to degrade over a time period of about 3 days to about 21 days, thereby producing an acidic byproduct having a pH lower than the initial pH of the wound, wherein the acidic byproduct reduces the initial pH of the wound to a target pH from about 4.0 to about 6.0.

2. The method of claim 1, wherein the initial pH of the wound is from about 7.0 to about 9.0.

3. The method of claim 1, wherein the acidic byproduct comprises an alpha-hydroxy acid.

4. The method of claim 1, wherein the fiber fragments form an aggregate.

5. The method of claim 4, wherein the aggregate of the fiber forms a shape selected from the group consisting of a spherical shape, an ellipsoidal shape, a globular shape, and a flattened cylindrical shape.

6. The method of claim 1, wherein the wound comprises a chronic wound.

7. The method of claim 1, wherein applying the scaffold to the wound comprises contacting the scaffold to at least a portion of the wound.

8. The method of claim 1, wherein applying the scaffold to the wound comprises implanting the scaffold within a body to make contact with the wound.

9. The method of claim 1, wherein applying the scaffold to the wound comprises directly contacting the scaffold to the wound.

10. The method of claim 1, wherein applying the scaffold to the wound comprises indirectly contacting the scaffold to the wound.

11. The method of claim 1, wherein the first electrospun polymer and the second electrospun polymer are co-electrospun with each other.

* * * * *